(12) United States Patent
Södervall et al.

(10) Patent No.: US 11,732,139 B2
(45) Date of Patent: Aug. 22, 2023

(54) USE OF A SUBSTRATE COATING FOR DECREASING LEAKAGE OF MATTER

(71) Applicant: Bactiguard AB, Tullinge (SE)

(72) Inventors: Billy Södervall, Markaryd (SE); Javier Sanchez, Spanga (SE)

(73) Assignee: BACTIGUARD AB, Tullinge (SE)

( * ) Notice: Subject to any disclaimer, the term of this patent is extended or adjusted under 35 U.S.C. 154(b) by 324 days.

(21) Appl. No.: 17/048,869

(22) PCT Filed: Apr. 24, 2019

(86) PCT No.: PCT/EP2019/060445
§ 371 (c)(1),
(2) Date: Oct. 19, 2020

(87) PCT Pub. No.: WO2019/206950
PCT Pub. Date: Oct. 31, 2019

(65) Prior Publication Data
US 2021/0238427 A1    Aug. 5, 2021

(30) Foreign Application Priority Data

Apr. 25, 2018  (SE) .................................. 1850493-6

(51) Int. Cl.
| | | |
|---|---|---|
| A61L 31/04 | (2006.01) | |
| A61L 17/14 | (2006.01) | |
| A61L 15/18 | (2006.01) | |
| A61L 27/30 | (2006.01) | |
| A61L 29/04 | (2006.01) | |
| A61L 17/06 | (2006.01) | |
| A61L 29/10 | (2006.01) | |
| A61L 27/16 | (2006.01) | |
| A61L 33/02 | (2006.01) | |
| A61L 31/08 | (2006.01) | |
| C09D 1/00 | (2006.01) | |
| A61L 17/10 | (2006.01) | |
| C09D 5/38 | (2006.01) | |
| C23C 28/02 | (2006.01) | |

(52) U.S. Cl.
CPC ............... *C09D 1/00* (2013.01); *A61L 17/06* (2013.01); *A61L 17/10* (2013.01); *A61L 27/165* (2013.01); *A61L 27/306* (2013.01); *A61L 29/042* (2013.01); *A61L 29/106* (2013.01); *A61L 31/049* (2013.01); *A61L 31/088* (2013.01); *A61L 33/022* (2013.01); *C09D 5/38* (2013.01); *C23C 28/023* (2013.01); *A61L 2300/802* (2013.01); *A61L 2430/12* (2013.01); *A61L 2430/20* (2013.01); *A61L 2430/24* (2013.01)

(58) Field of Classification Search
CPC .. C09D 1/00; C09D 5/38; A61L 17/10; A61L 27/165; A61L 27/306; A61L 29/042; A61L 29/106; A61L 31/049; A61L 31/088; A61L 33/022; A61L 2300/802; A61L 2430/12; A61L 2430/20; A61L 2430/24; C23C 28/023
See application file for complete search history.

(56) References Cited

U.S. PATENT DOCUMENTS

| | | | |
|---|---|---|---|
| 5,355,898 A | * | 10/1994 | Ripamonti |
| 6,224,983 B1 | | 5/2001 | Sodervall et al. |
| 2009/0210068 A1 | | 8/2009 | Zeller et al. |
| 2018/0104385 A1 | | 4/2018 | Ohrlander et al. |

FOREIGN PATENT DOCUMENTS

| | | |
|---|---|---|
| EP | 2007440 B1 | 1/2014 |
| JP | H06125922 A | 5/1994 |
| JP | H11238607 A | 8/1999 |
| JP | 2001192486 | 7/2001 |
| JP | 2001192486 A | 7/2001 |
| JP | 2017202023 | 11/2017 |
| RU | 2286400 C1 | 10/2006 |
| RU | 2325191 C1 | 5/2008 |
| RU | 2540227 C2 | 2/2015 |
| RU | 2580281 C1 | 4/2016 |
| RU | 2633723 C2 | 10/2017 |

(Continued)

OTHER PUBLICATIONS

Thomas, P. & Summer, Burkhard. (2011). Implant allergy. Allergologie. 34. 42-48. 10.5414/ALX01394E.
McLucas, E., Rochev, Y., Carroll, W.M. et al. Analysis of the effects of surface treatments on nickel release from nitinol wires and their impact on candidate gene expression in endothelial cells. J Mater Sci: Mater Med 19, 975-980 (2008).
International Preliminary Report on Patentability for PCT Application No. PCT/EP2019/060445 dated Oct. 27, 2020.
International Search Report for PCT Application No. PCT/EP2019/060445 dated Jul. 25, 2019.
Written Opinion for PCT Application No. PCT/EP2019/060445 dated Oct. 27, 2020.

(Continued)

*Primary Examiner* — Alma Pipic
(74) *Attorney, Agent, or Firm* — Branch Partners PLLC; Bruce E. Black

(57) ABSTRACT

There is provided a method for decreasing leakage of matter from an object to a surrounding, said object being coated with a coating at least partially applied on the object, said coating comprising an at least partially covering layer comprising silver, said object optionally comprising area(s) without said layer, said coating comprising metal particles applied on the layer and optionally on areas without said layer, said metal particles comprising palladium and at least one metal selected from the group consisting of gold, ruthenium, rhodium, osmium, iridium, niobium, neodymium and platinum and wherein the amount of the metal particles is in the interval 0.01-8 µg/cm$^2$. Advantages include that leakage of matter such as latex allergens of metal ions can be reduced while the coating is both biocompatible and antimicrobial. Further, the blood clotting can be reduced.

29 Claims, 10 Drawing Sheets

(56) References Cited

FOREIGN PATENT DOCUMENTS

| WO | WO9518637 | 7/1995 |
| WO | WO9740209 | 10/1997 |
| WO | 2007/087269 | 8/2007 |
| WO | 2007/117191 | 10/2007 |
| WO | 2007/117213 | 10/2007 |
| WO | 2007/117214 | 10/2007 |
| WO | 2007/142579 | 12/2007 |
| WO | WO2008/092435 A2 | 8/2008 |
| WO | WO2014147885 | 9/2014 |
| WO | 2014/168712 | 10/2014 |

OTHER PUBLICATIONS

Baun, W., Walter, U., Holbein, R., & Thull, R. (2005). Elektrochemische Eigenschaften biokompatibler Hartstorfmodifikationen auf Titan und Stahl bei mechanischer Belastung / Electrochemical properties of biocompatible metal modifications on titanium and steel under mechanical loads Biomedizinische Technik / Biomedical Engineering, 50(4), 100-106.

Song J, Wang L, Zibart A, Koch C. Corrosion Protection of Electrically Conductive Surfaces. Metals. 2012; 2(4):450-477.

Viennot, S. "Corrosion resistance of colbalt-chromium and palladium-silver alloys used in fixed prosthetic restorations" In: Eur. J. Oral Sci., Feb. 2005, vol. 113, pp. 90-95.

\* cited by examiner

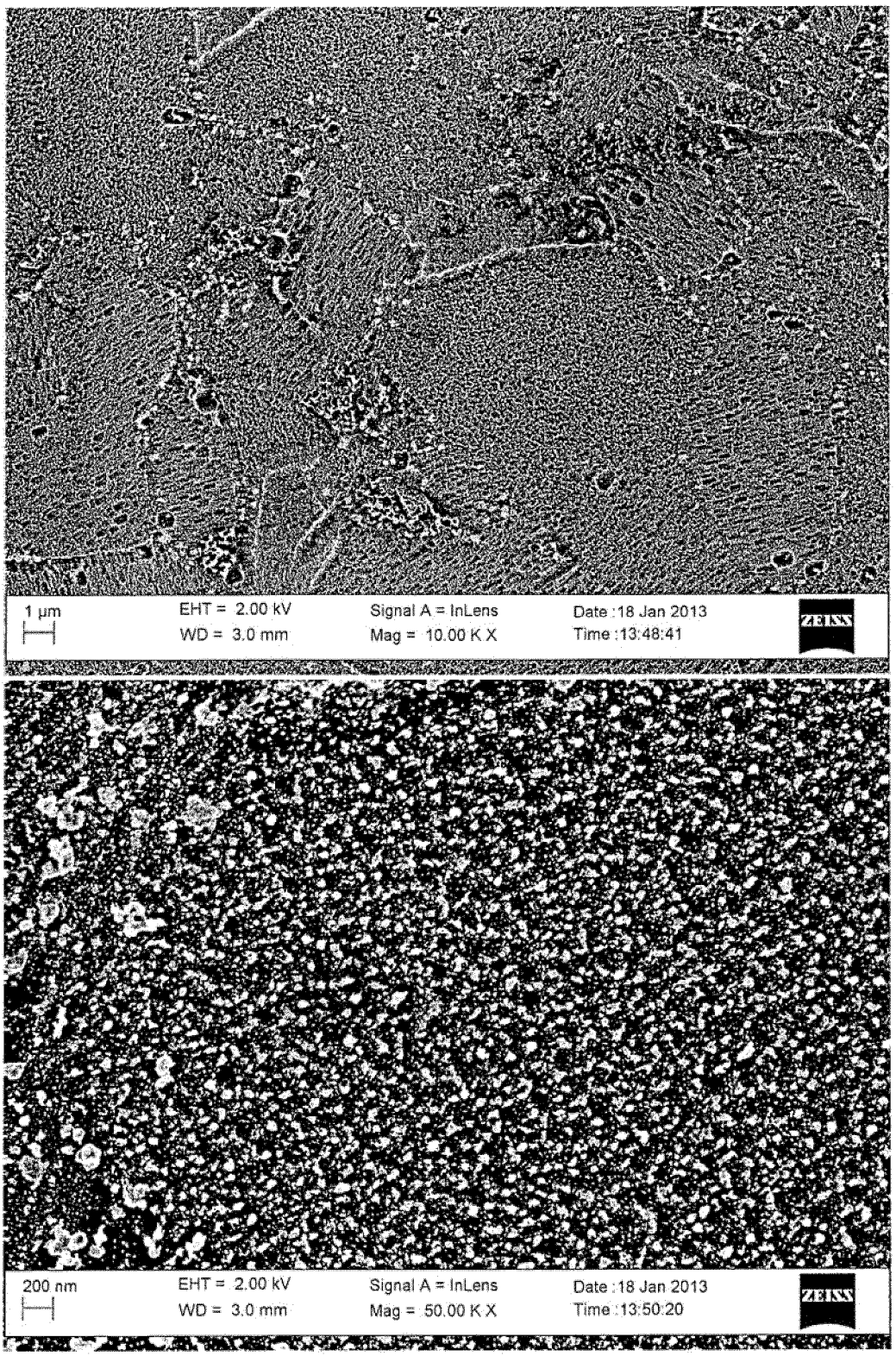
Fig 1a(top) and b(bottom)

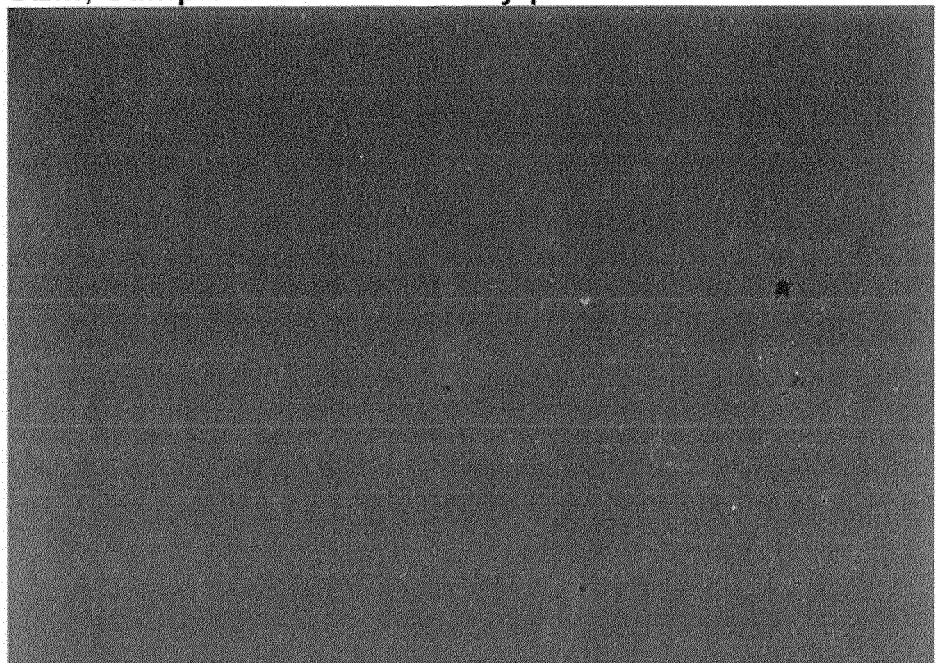
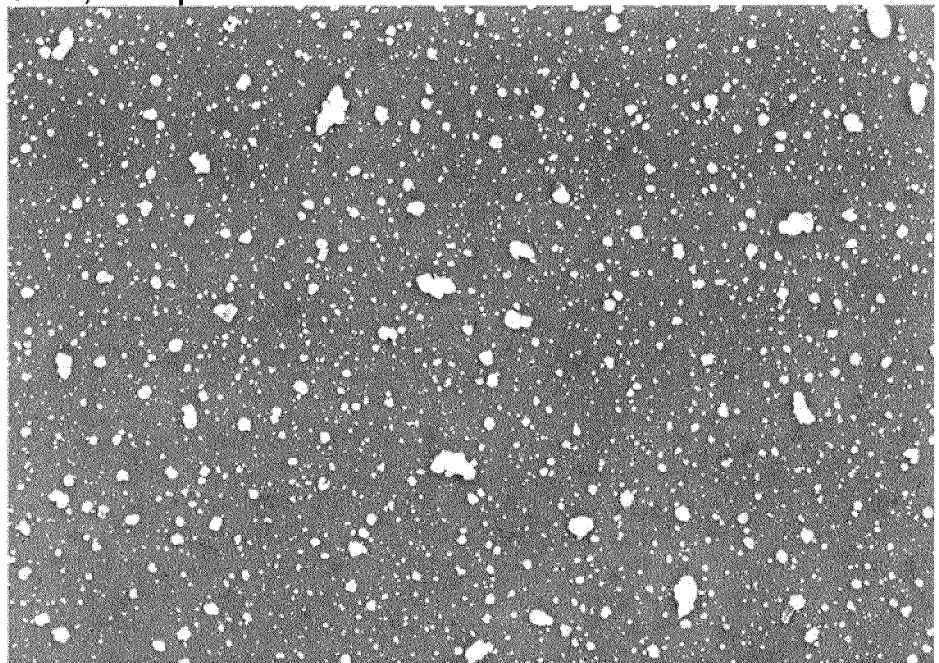
Fig 2a(top) and b(bottom)

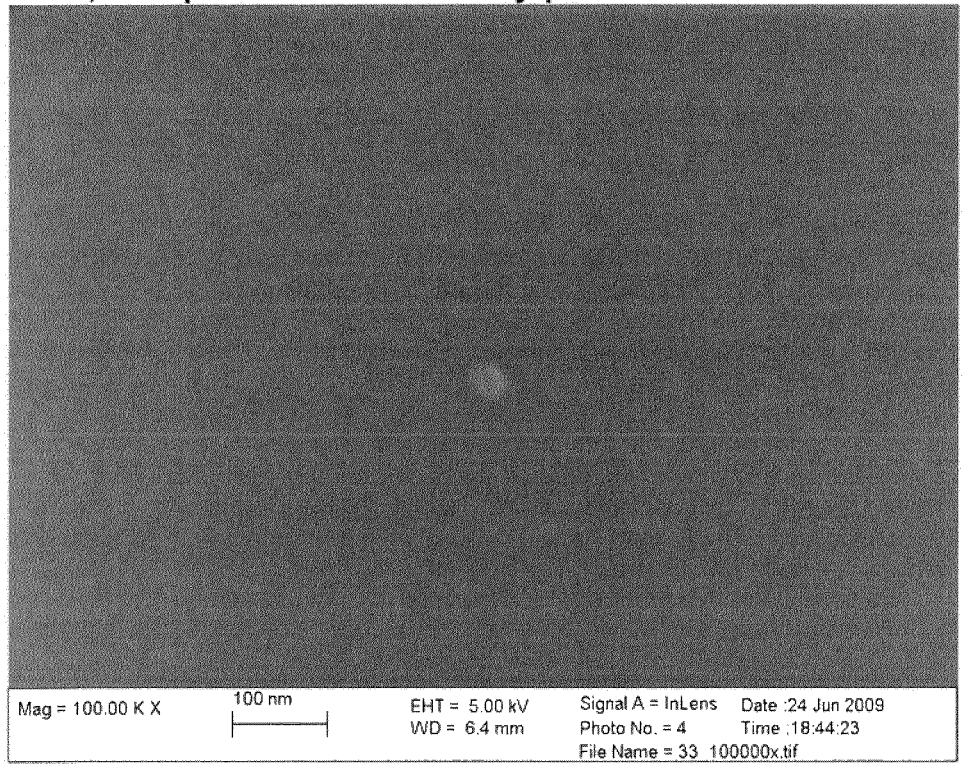
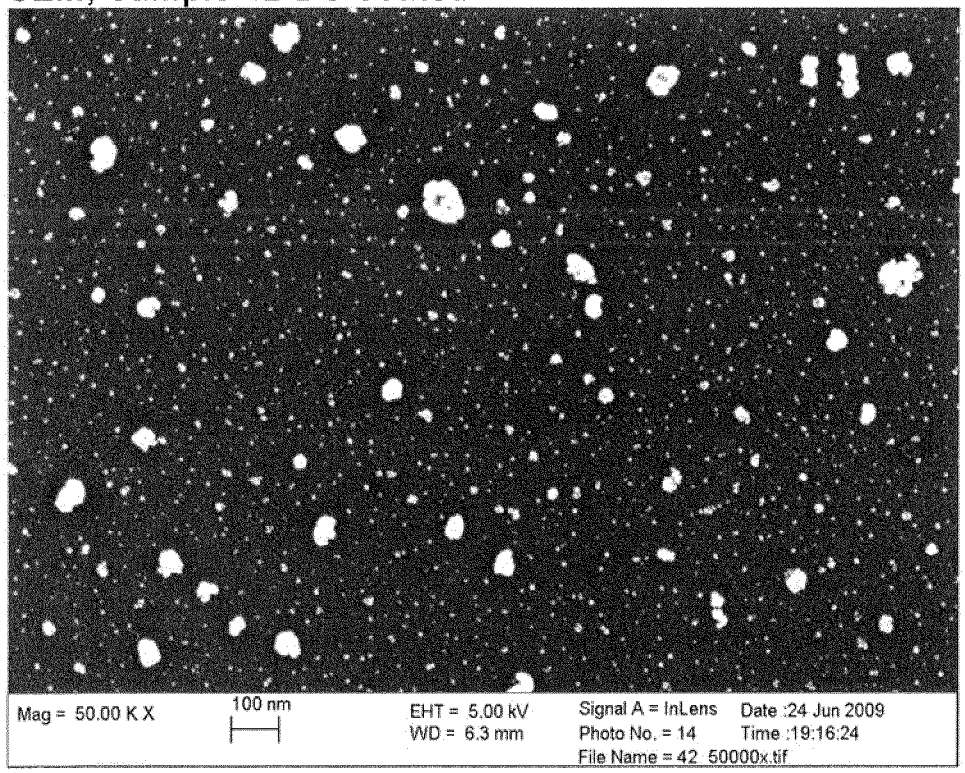
Fig 2c(top) and d(bottom)

USE OF A SUBSTRATE COATING FOR DECREASING LEAKAGE OF MATTER

CROSS-REFERENCE TO RELATED APPLICATIONS

This present application is a U.S. national stage application of PCT Application No. PCT/EP2019/060445, filed Apr. 24, 2019, which claims priority to Swedish Patent Application No. 1850493-6 filed Apr. 25, 2018, both of which are hereby incorporated by reference in their entirety.

FIELD OF THE INVENTION

The present invention relates to a new use of a surface coating for minimizing the leakage of various substances from the coated object. The coating is both antimicrobial and displays biocompatible properties not least with respect to blood clotting.

BACKGROUND

Surfaces with antimicrobial and biocompatible properties are important within many applications. Examples of surfaces where such properties are of importance include surfaces intended to be in contact with a human or animal body including contact with the skin as well as body cavities and inside a body.

It is known in the art that leakage of substances from polymers including for instance from gloves made of for instance latex or other polymeric materials is a problem regarding for instance allergies. The substances leaking may cause allergies to sensitive persons. Latex allergy increased in the 1980s when healthcare workers began to use latex gloves.

Another example is leakage of metals from metals and metal alloys. One example is leakage of Ni from alloys comprising Ni, such as nitinol and other alloys. Another problem is leakage of Ti from Ti-metal and Ti-alloys.

E. Lucas et al in J. Mater Sci: Mater Med (2008) 19:975-980 discloses nickel release form nitinol wires and found that E-selectin which is a marker for endothelial cell injury was upregulated in cells that were incubated with nitinol wires that release the highest amount of nickel.

Although the amount of substances leaking from polymeric materials or metals is very low, the very small amounts may cause problems regarding for instance allergies as well as other problems. Such problems are individual, for some individuals a certain level of leaked substances may not cause any harm, whereas the same level of the same substances may cause problems and symptoms for another individual. As a precaution, it is thus desirable to keep all leakage of substances as low as possible.

In summary leakage of matter including but not limited to metal ions and various compounds from polymers as well as metals and metal alloys is a problem and it is desirable to minimize such leakage. In general it is desirable to keep any leakage as low as possible as a precaution.

U.S. Pat. No. 6,224,983 discloses an article with an adhesive, antimicrobial and biocompatible coating comprising a layer of silver stabilised by exposure to one or more salts of one or more metals selected from the group consisting of platinum, palladium, rhodium, iridium, ruthenium and osmium. The thickness of the silver layer is in the range 2-2000 Å (Å, Ångström, Angstrom, $10^{-10}$ m) and further disclosed ranges are 2-350 Å and 2-50 Å. There are also examples of a thickness of the silver layer of 50 Å, 350 Å, 500 Å, and 1200 Å. The substrate may be latex, polystyrene, polyester, polyvinylchloride, polyurethane, ABS polymers, polycarbonate, polyamide, polytetrafluoroethylene, polyimide or synthetic rubber.

WO2007/117191, WO2007/117213 and WO2007/117214 disclose a substrate having an electron donating surface, characterized in that there are metal particles on said surface, the metal particles comprise palladium and at least one metal selected from the group consisting of gold, ruthenium, rhodium, osmium, iridium, and platinum and wherein the amount of the metal particles is from about 0.001 to about 8 $\mu g/cm^2$.

WO 2007/142579 discloses a polymer matrix, characterized in that it comprises a. an electron donating constituent and b. metal particles comprising at least one metal selected from the group consisting of palladium, gold, ruthenium, rhodium, osmium, iridium, and platinum.

In general, for objects used in contact with humans or animals, it is desired to increase the antimicrobial and antimicrobial properties of the surface of the object, while it is still biocompatible.

A problem in the state of the art is how to minimize the leakage of various substances and elements from a surface. Another issue for some applications is how to reduce the blood clotting on man-made materials in contact with blood.

Regarding the leakage and reduction of leakage of substances from objects in contact with a human or animal body, it is desired to minimize it even if it does not cause any symptoms or negative effects. The leakage of various substances should be minimized as a general precautionary principle.

SUMMARY

One object of the present invention is to obviate at least some of the disadvantages in the prior art and provide use of a surface coating for decreasing leakage of matter from the object to a surrounding.

In a first aspect there is provided use of a surface coating, said coating is at least partially applied on an object, said coating comprising an at least partially covering layer comprising silver, said object optionally comprising area(s) without said layer, said coating comprising metal particles applied on the layer and optionally on areas without said layer, said metal particles comprising palladium and at least one metal selected from the group consisting of gold, ruthenium, rhodium, osmium, iridium, niobium, neodymium and platinum and wherein the amount of the metal particles is in the interval 0.01-8 $\mu g/cm^2$, for decreasing leakage of matter from the object to a surrounding.

In a second aspect there is provided a method for decreasing leakage of matter from an object to a surrounding, said object being coated with a coating at least partially applied on the object, said coating comprising an at least partially covering layer comprising silver, said object optionally comprising area(s) without said layer, said coating comprising metal particles applied on the layer and optionally on areas without said layer, said metal particles comprising palladium and at least one metal selected from the group consisting of gold, ruthenium, rhodium, osmium, iridium, niobium, neodymium and platinum and wherein the amount of the metal particles is in the interval 0.01-8 $\mu g/cm^2$.

In a third aspect there is provided use of a surface coating for at least one of preventing, alleviating and treating symptoms at least partially caused by leakage from an object, said coating is at least partially applied on an object, said coating comprising an at least partially covering layer comprising silver, said object optionally comprising area(s) without said layer, said coating comprising metal particles applied on the layer and optionally on areas without said layer, said metal particles comprising palladium and at least one metal selected from the group consisting of gold, ruthenium, rhodium, osmium, iridium, niobium, neodymium and platinum and wherein the amount of the metal particles is in the interval 0.01-8 µg/cm².

In a fourth aspect there is provided a surface coating for use in at least one of prevention, alleviation and treatment of symptoms at least partially caused by leakage from an object, said coating is at least partially applied on the object, said coating comprising an at least partially covering layer comprising silver, said object optionally comprising area(s) without said layer, said coating comprising metal particles applied on the layer and optionally on areas without said layer, said metal particles comprising palladium and at least one metal selected from the group consisting of gold, ruthenium, rhodium, osmium, iridium, niobium, neodymium and platinum and wherein the amount of the metal particles is in the interval 0.01-8 µg/cm².

In a fifth aspect there is provided use of a surface coating for coating a surface for decreasing leakage of matter from an object to a surrounding, said coating is at least partially applied on the object, said coating comprising an at least partially covering layer comprising silver, said object optionally comprising area(s) without said layer, said coating comprising metal particles applied on the layer and optionally on areas without said layer, said metal particles comprising palladium and at least one metal selected from the group consisting of gold, ruthenium, rhodium, osmium, iridium, niobium, neodymium and platinum and wherein the amount of the metal particles is in the interval 0.01-8 µg/cm².

In a sixth aspect there is provided a method for decreasing blood clotting in human or animal blood caused by an object, said object being coated with a coating at least partially applied on the object, said coating comprising an at least partially covering layer comprising silver, said object optionally comprising area(s) without said layer, said coating comprising metal particles applied on the layer and optionally on areas without said layer, said metal particles comprising palladium, neodymium and optionally at least one metal selected from the group consisting of gold, ruthenium, rhodium, osmium, iridium, niobium, and platinum and wherein the amount of the metal particles is in the interval 0.01-8 µg/cm².

In a seventh aspect there is provided a method for reducing microbial growth on an object, said object being coated with a coating at least partially applied on the object, said coating comprising an at least partially covering layer comprising silver, said object optionally comprising area(s) without said layer, said coating comprising metal particles applied on the layer and optionally on areas without said layer, said metal particles comprising palladium, neodymium and optionally at least one metal selected from the group consisting of gold, ruthenium, rhodium, osmium, iridium, niobium, and platinum and wherein the amount of the metal particles is in the interval 0.01-8 µg/cm².

In an eighth aspect there is provided use of a surface coating, said coating is at least partially applied on an object, said coating comprising an at least partially covering layer comprising silver, said object optionally comprising area(s) without said layer, said coating comprising metal particles applied on the layer and optionally on areas without said layer, said metal particles comprising palladium and neodymium and optionally at least one metal selected from the group consisting of gold, ruthenium, rhodium, osmium, iridium, niobium, and platinum and wherein the amount of the metal particles is in the interval 0.01-8 µg/cm², for decreasing blood clotting in human or animal blood caused by the object.

In a ninth aspect there is provided use of a surface coating, said coating is at least partially applied on an object, said coating comprising an at least partially covering layer comprising silver, said object optionally comprising area(s) without said layer, said coating comprising metal particles applied on the layer and optionally on areas without said layer, said metal particles comprising palladium and neodymium and optionally at least one metal selected from the group consisting of gold, ruthenium, rhodium, osmium, iridium, niobium, and platinum and wherein the amount of the metal particles is in the interval 0.01-8 µg/cm², for reducing microbial growth on the object.

In a tenth aspect there is provided an object at least partially coated with a surface coating, said coating comprising an at least partially covering layer comprising silver, said object optionally comprising area(s) without said layer, said coating comprising metal particles applied on the layer and optionally on areas without said layer, said metal particles comprising palladium and neodymium and optionally at least one metal selected from the group consisting of gold, ruthenium, rhodium, osmium, iridium, niobium, and platinum and wherein the amount of the metal particles is in the interval 0.01-8 µg/cm².

The first to fifth aspects include metal particles comprising palladium and at least one other metal according to the claims. The sixth to tenth aspects include metal particles comprising both palladium and neodymium and further optional metals according to the claims.

Further embodiments of the present invention are defined in the appended dependent claims, which are explicitly incorporated herein.

One advantage is that leakage of various substances from coated objects is reduced while the coating is both biocompatible and antimicrobial. In some aspects, the coating is comparable to a coating that acts as a barrier to decrease leakage of matter from a coated object. In other aspects, the antimicrobial effect is improved.

BRIEF DESCRIPTION OF THE DRAWINGS

Aspects and embodiments will be described with reference to the following drawings in which:

FIG. 1a shows a representative electron micrograph of an uncoated surface of titanium in about 10000 times magnification. FIG. 1b shows the same titanium surface with a coating according to the invention in about 50000 times magnification.

FIG. 2a shows a representative electron micrograph of an uncoated surface of an object of a medical grade silicone. 2b shows the same type of surface where the layer and the metal particles have been added. The magnification is about 20000 times.

FIG. 2c shows a representative electron micrograph of an uncoated sample. The object is made of medical grade silicone. Magnification about 100000 times. FIG. 2d shows the same type of surface where the layer and the metal particles have been added. The magnification is about 50000 times.

DETAILED DESCRIPTION

Figure 3A:
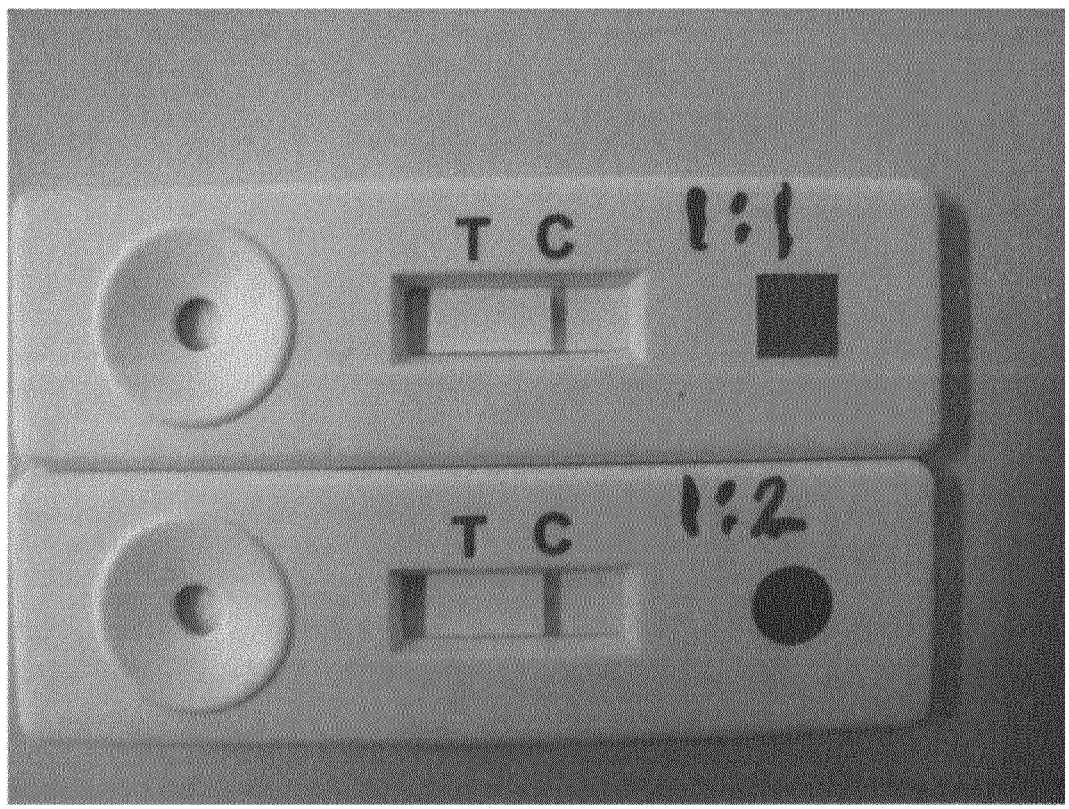
FIG. 3a-c show the result of allergen testing on latex foley catheters.

Before the invention is disclosed and described in detail, it is to be understood that this invention is not limited to particular configurations, process steps and materials disclosed herein as such configurations, process steps and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

The following terms are used throughout the description and the claims.

"Amount" of particles or other material on a surface is herein often given as $\mu g/cm^2$. This is a suitable way of expressing the amount since the applied layer is very thin. For calculating the amount, the area of the object is measured and the amount per area is calculated.

"Antimicrobial" as used herein is the property of suppressing or eliminating microbial growth. Microbial growth includes but is not limited to bacterial growth.

"Biocompatible" as used herein is the ability of a material to perform with an appropriate host response in a specific application.

The phrase "at least one of prevention, alleviation and treatment of symptoms" as used herein is means one or more of: measures taken for prevention of diseases or symptoms as a precaution, measures taken for alleviating symptoms, and measures taken for treating symptoms. It relates to symptoms of a human or an animal. A human or animal individual can be subject of the prevention, alleviation and/or treatment. For preventing symptoms, it is not necessary that there exists an increased risk for symptoms; it can always be used as a precaution to reduce the probability that an individual may display symptoms. Prevention can also be used for a healthy individual. Alleviating symptoms is when the symptoms may not disappear completely, but are reduced to a higher or lower degree. Treating a symptom is when the symptoms are treated by the reduced leakage, as part of appropriate medical care for a human or animal individual in need thereof. A treatment may not necessarily remove all symptoms, although this can be the case. The symptoms refer to any symptoms caused by leakage of matter from an object.

"Object" as used herein is the base, which is treated and at least partially surface coated according to the present invention.

According to the present invention, a surface coating is applied on an object to give it desired properties. The object can be made of a wide range of materials.

In a first aspect there is provided use of a surface coating, said coating is at least partially applied on an object, said coating comprising an at least partially covering layer comprising silver, said object optionally comprising area(s) without said layer, said coating comprising metal particles applied on the layer and optionally on areas without said layer, said metal particles comprising palladium and at least one metal selected from the group consisting of gold, ruthenium, rhodium, osmium, iridium, niobium, neodymium and platinum and wherein the amount of the metal particles is in the interval 0.01-8 $\mu g/cm^2$, for decreasing leakage of matter from the object to a surrounding.

In one embodiment, the layer comprises silver in an amount in the interval 0.05-12 $\mu g/cm^2$. In one embodiment, the layer comprises silver in an amount in the interval 0.05-8 $\mu g/cm^2$. In one embodiment, the layer comprises silver in an amount in the interval 0.05-4 $\mu g/cm^2$. In one embodiment, the layer comprises silver in an amount below 8 $\mu g/cm^2$.

The at least partially covering layer comprising silver can be applied in different ways. In one embodiment, the layer is applied patch-wise. In one embodiment, the layer is applied as particles on the surface. In one embodiment, the layer is applied as a completely covering layer.

In one embodiment, the object comprises at least one metal. In one embodiment, the at least one metal is selected from the group consisting of stainless steel, medical grade steel, titanium, medical grade titanium, cobalt, nickel, chromium, and mixtures thereof. In one embodiment, the at least one metal is an alloy comprising nickel and titanium.

In one embodiment, the object comprises at least one polymer. In one embodiment, the polymer is selected from the group consisting of latex, vinyl, polymers comprising vinyl groups, polyurethane urea, silicone, polyvinylchloride, polypropylene, styrene, polyurethane, polyester, copolymerisates of ethylene vinyl acetate, polytetrafluoroethylene (PTFE), polyether ether ketone (PEEK), polystyrene, polycarbonate, polyethylene, polyacrylate, polymethacrylate, acrylonitrile butadiene styrene (ABS), polyamide, polyimide, and mixtures thereof. In one embodiment, the polymer is latex.

In one embodiment, the object comprises at least one selected from apatite and hydroxyapatite.

It must be noted that the metal particles are essentially homogenously composed, i.e. they have essentially the same composition of metals throughout the particle. For instance, a metal particle comprising palladium and gold is an alloy of the metals.

In one embodiment, the amount of the metal particles is in the interval 0.01-4 $\mu g/cm^2$.

In one embodiment, the amount of metal particles is 10-30% of the amount of silver in the layer, calculated by weight. The amount of metal particles is calculated as the weight of the particles for a certain area, the amount of silver is calculated as the weight of the silver for the same area, and then the relationship is calculated. The calculation by weight is made for a certain area on the coated object.

In one embodiment, the metal particles are separate particles, not in contact with each other.

In one embodiment, the ratio of palladium to non-palladium metals in the metal particles is from about 0.01:99.99 to about 99.99:0.01. In one embodiment, the ratio of palladium to non-palladium metals in the metal particles is from about 0.5:99.5 to about 99.8:0.2. In one embodiment, the ratio of palladium to non-palladium metals in the metal particles is from about 2:98 to about 95:5. The particles must always comprise palladium. In addition to palladium there is at least one other metal. A ratio of palladium to other metals in the metal particles of from about 0.01:99.99 to about 99.99:0.01 can be used in the present invention. A ratio from about 0.5:99.5 to about 99.8:0.2 is used in one embodiment. In one embodiment ratio is from about 2:98 to about 95:5. In another embodiment, the ratio is in the interval from 5:95 to 95:5. In another embodiment, the ratios are from about 10:90 to about 90:10. A person skilled in the art realises that the ration also can be in other intervals. Examples of other ranges for the ratio include but are not limited to: 0.01:99.99 to 0.05:99.95, 0.05:99.95 to 0.1:99.9, 0.1:99.9 to 0.5:99.5, 0.5:99.5 to 1:99, 1:99 to 2:98, 2:98 to 4:96, 4:96 to 6:94, 6:94 to 8:92, 8:92 to 10:90, 10:90 to 20:80, 20:80 to 30:70, 30:70 to 40:60, 40:60 to 50:50, 50:50 to 60:40, 60:40 to 70:30, 70:30 to 80:20, 80:20 to 90:10, 90:10 to 92:8, 92:8 to 94:6, 94:6 to 96:4, 96:4 to 98:2, 98:2 to 99:1, 99:1 to 99.5:0.5, 99.5:0.5 to 99.9:0.1 to 99.95:0.05, 99.95:0.05 to 99.99:0.01

In one embodiment, the metal particles, in addition to palladium, comprise gold.

In one embodiment, the metal particles, in addition to palladium, comprise niobium. In one embodiment, the metal particles, in addition to palladium, comprise neodymium, wherein the neodymium is present in an amount corresponding to 0.002-0.5 µg/cm$^2$. In one embodiment, the metal particles consist of only palladium and neodymium. In one embodiment the metal particles comprise, palladium, gold and neodymium. In one embodiment the metal particles in addition to palladium, comprise gold so that the ratio calculated by weight between palladium and gold is in the interval 0.8-1.2. It has turned out that when the metal particles comprise palladium and neodymium then the surface coating is particularly suited for preventing blood clotting if the surface is exposed to blood from a human or animal. A weight ratio between gold and palladium in the interval 0.8-1.2, i.e. about equal weight parts is in one embodiment used to counteract blood clotting. In another embodiment, only a relatively small addition of neodymium to the particles is added to promote the reduction of thrombosis, such as 0.02 to 0.5 µg/cm$^2$. Blood clotting refers to the complex process when blood coagulates and forms a gel. It includes but is not limited to fibrinogen formation, In one embodiment, the metal particles, in addition to palladium, comprise rhodium. If the decrease of leakage of matter is more important than the antimicrobial properties, then rhodium can be chosen together with palladium since rhodium gives very good results to prevent leakage of matter, but slightly lower antimicrobial effect of the coating in some cases. In other cases, the antimicrobial effect is not lower. The decrease of leakage of matter is in the case of metal most often the same as decrease of corrosion. For metals ions leaking out of the metal or alloy means corrosion. Thus in one embodiment the coated object is a metal or metal alloy and the coating comprises silver and in addition particles comprising palladium and rhodium. In one embodiment, the particles consist only of palladium and rhodium. In one embodiment, the amount of rhodium corresponds to 0.05-2 µg/cm$^2$.

In one embodiment, the metal particles have a size in the interval 10-10000 Å. In one embodiment, the metal particles have a size in the interval 100-600 Å. A person skilled in the art realises that the particle size can be in different intervals within from about 10 to about 10000 Å. Examples of such intervals include but are not limited to 10-8000 Å, 10-6000 Å, 10-4000 Å, 10-2000 Å, 10-1000 Å, 10-100 Å, 100-10000 Å, 1000-10000 Å, 2000-10000 Å, 4000-10000 Å, 6000-10000 Å, 8000-10000 Å, 100-1000 Å, 1000-2000 Å, 2000-4000 Å, 4000-6000 Å, 6000-8000 Å, 1000-5000 Å, and 5000-8000 Å.

In one embodiment, the object is at least one selected from the group consisting of a catheter, a glove, an implant, a pacemaker, a stent, a dental implant, a rupture net, a surgical instrument, a blood bag, an artificial heart valve, a central venous catheter, a peripheral venous catheter, a vascular port, a haemodialysis equipment, a peritoneal dialysis equipment, a plasmapheresis device, an inhalation drug delivery device, a vascular graft, a cardiac assist device, a wound dressing, an intermittent catheter, an ECG electrode, a peripheral stent, a bone replacing implant, an orthopaedic implant, an orthopaedic device, a tissue replacing implant, an intraocular lens, a suture, a needle, a drug delivery device, an endotracheal tube, a shunt, a drain, a suction device, a hearing aid device, an urethral medical device, an artificial blood vessel. Examples of objects comprising a substrate according to the present invention include but are not limited to medical devices, medical instruments, disposable articles, medical disposable articles. Further examples of objects comprising a substrate coated according to the present invention include but are not limited to contact lenses, pacemakers, pacemaker electrodes, stents (bare metal and drug eluting), dental implants, rupture nets, rupture mesh, blood centrifuge equipment (in contact with blood), surgical instruments, gloves, blood bags, artificial heart valves, central venous catheters, peripheral venous catheters, vascular ports, haemodialysis equipment, peritoneal dialysis equipment, plasmapheresis devices, inhalation drug delivery devices, vascular grafts, arterial grafts, cardiac assist devices, wound dressings, intermittent catheters, ECG electrodes, peripheral stents, bone replacing implants, orthopaedic implants, orthopaedic devices (screws, pins, staples, suture anchors etc.), tissue replacing implants, intraocular lenses, sutures, needles, drug delivery devices, endotracheal tubes, shunts, drains, suction devices, hearing aid devices, urethral medical devices, and artificial blood vessels.

In one embodiment, the amount of the metal particles is from about 0.01 to about 4 µg/cm$^2$. In another embodiment, the amount of the metal particles is from about 0.01 to about 1 µg/cm$^2$. Examples of ranges within from about 0.001 to about 8 µg/cm$^2$ include but are not limited to 0.001-6, 0.001-4, 0.001-2, 0.001-1, 0.001-0.5, 0.001-0.25, 0.001-0.15, 0.15-8, 0.25-8, 0.5-8, 1-8, 2-8, 4-8, 6-8, 0.15-0.25, 0.25-0.5, 0.5-1, 1-2, 2-4, 4-6, 1-3, and 3-6 µg/cm$^2$.

The coating should be applied at least partially on some kind of object in order to be usable.

The first layer is also referred to as just "the layer". In one embodiment, silver is applied as a first layer on the object as patches, i.e. a layer which does not cover the entire surface of the object and leaves some parts of the uncoated surface exposed. In one embodiment, silver is applied as a fully covering coating. Silver is in one embodiment applied in an amount in the interval 0.05-12 µg/cm$^2$. The amount of silver can also be within other ranges as long as the amount is in the range 0.05-12 µg/cm$^2$. Examples of such other ranges include but are not limited to 0.05-10, 0.05-8, 0.05-6, 0.05-4, 0.05-2, 0.05-1, 0.05-0.5, 0.05-0.25, 0.05-0.15, 0.15-12, 0.25-12, 0.5-12, 1-12, 2-12, 4-12, 6-12, 8-12, 10-12, 0.15-0.25, 0.25-0.5, 0.5-1, 1-2, 2-4, 4-6, 6-8, 8-10, 1-5, and 5-10 µg/cm$^2$. An applied layer of silver is in one embodiment applied so that it is uniform, essentially without agglomerates or clusters on the surface. In an alternative embodiment, the applied layer of silver is not uniform and is not completely covering the object that is coated. If the silver layer is homogenous and uniform, the applied amount in µg/cm$^2$ may be converted to a thickness in Å. In one embodiment of the present invention, the silver is a layer of commercially available essentially pure silver, which does not exclude the possibility of small amounts of impurities.

In a second aspect there is provided a method for decreasing leakage of matter from an object to a surrounding, said object being coated with a coating at least partially applied on the object, said coating comprising an at least partially covering layer comprising silver, said object optionally comprising area(s) without said layer, said coating comprising metal particles applied on the layer and optionally on areas without said layer, said metal particles comprising palladium and at least one metal selected from the group consisting of gold, ruthenium, rhodium, osmium, iridium, niobium, neodymium and platinum and wherein the amount of the metal particles is in the interval 0.01-8 µg/cm$^2$. The embodiments of the first aspect are also applicable to the second aspect.

In a third aspect there is provided use of a surface coating for at least one of preventing, alleviating and treating symptoms at least partially caused by leakage from an object, said coating is at least partially applied on an object, said coating comprising an at least partially covering layer comprising silver, said object optionally comprising area(s) without said layer, said coating comprising metal particles applied on the layer and optionally on areas without said layer, said metal particles comprising palladium and at least one metal selected from the group consisting of gold, ruthenium, rhodium, osmium, iridium, niobium, neodymium and platinum and wherein the amount of the metal particles is in the interval 0.01-8 µg/cm$^2$.

In a fourth aspect there is provided a surface coating for use in at least one of prevention, alleviation and treatment of symptoms at least partially caused by leakage from an object, said coating is at least partially applied on the object, said coating comprising an at least partially covering layer comprising silver, said object optionally comprising area(s) without said layer, said coating comprising metal particles applied on the layer and optionally on areas without said layer, said metal particles comprising palladium and at least one metal selected from the group consisting of gold, ruthenium, rhodium, osmium, iridium, niobium, neodymium and platinum and wherein the amount of the metal particles is in the interval 0.01-8 µg/cm$^2$.

In a fifth aspect there is provided use of a surface coating for coating a surface for decreasing leakage of matter from an object to a surrounding, said coating is at least partially applied on the object, said coating comprising an at least partially covering layer comprising silver, said object optionally comprising area(s) without said layer, said coating comprising metal particles applied on the layer and optionally on areas without said layer, said metal particles comprising palladium and at least one metal selected from the group consisting of gold, ruthenium, rhodium, osmium, iridium, niobium, neodymium and platinum and wherein the amount of the metal particles is in the interval 0.01-8 µg/cm$^2$.

In a sixth aspect there is provided a method for decreasing blood clotting in human or animal blood caused by an object, said object being coated with a coating at least partially applied on the object, said coating comprising an at least partially covering layer comprising silver, said object optionally comprising area(s) without said layer, said coating comprising metal particles applied on the layer and optionally on areas without said layer, said metal particles comprising palladium, neodymium and optionally at least one metal selected from the group consisting of gold, ruthenium, rhodium, osmium, iridium, niobium, and platinum and wherein the amount of the metal particles is in the interval 0.01-8 µg/cm$^2$. All embodiments in the present description can be combined with this aspect. The addition of neodymium has the advantage of improving the effect of decreasing the blood clotting.

In a seventh aspect there is provided a method for reducing microbial growth on an object, said object being coated with a coating at least partially applied on the object, said coating comprising an at least partially covering layer comprising silver, said object optionally comprising area(s) without said layer, said coating comprising metal particles applied on the layer and optionally on areas without said layer, said metal particles comprising palladium, neodymium and optionally at least one metal selected from the group consisting of gold, ruthenium, rhodium, osmium, iridium, niobium, and platinum and wherein the amount of the metal particles is in the interval 0.01-8 µg/cm$^2$. All embodiments in the present description can be combined with this aspect. The addition of neodymium has the advantage of improving the effect of decreasing the blood clotting.

In an eighth aspect there is provided use of a surface coating, said coating is at least partially applied on an object, said coating comprising an at least partially covering layer comprising silver, said object optionally comprising area(s) without said layer, said coating comprising metal particles applied on the layer and optionally on areas without said layer, said metal particles comprising palladium and neodymium and optionally at least one metal selected from the group consisting of gold, ruthenium, rhodium, osmium, iridium, niobium, and platinum and wherein the amount of the metal particles is in the interval 0.01-8 µg/cm$^2$, for decreasing blood clotting in human or animal blood caused by the object. All embodiments in the present description can be combined with this aspect. The addition of neodymium has the advantage of improving the effect of decreasing the blood clotting.

In a ninth aspect there is provided use of a surface coating, said coating is at least partially applied on an object, said coating comprising an at least partially covering layer comprising silver, said object optionally comprising area(s) without said layer, said coating comprising metal particles applied on the layer and optionally on areas without said layer, said metal particles comprising palladium and neodymium and optionally at least one metal selected from the group consisting of gold, ruthenium, rhodium, osmium, iridium, niobium, and platinum and wherein the amount of the metal particles is in the interval 0.01-8 µg/cm$^2$, for reducing microbial growth on the object. All embodiments in the present description can be combined with this aspect. The addition of neodymium has also the advantage of improving the reduction of microbial growth in addition to decreasing the blood clotting.

In a tenth aspect there is provided an object at least partially coated with a surface coating, said coating comprising an at least partially covering layer comprising silver, said object optionally comprising area(s) without said layer, said coating comprising metal particles applied on the layer and optionally on areas without said layer, said metal particles comprising palladium and neodymium and optionally at least one metal selected from the group consisting of gold, ruthenium, rhodium, osmium, iridium, niobium, and platinum and wherein the amount of the metal particles is in the interval 0.01-8 µg/cm$^2$. All embodiments in the present description can be combined with this aspect. The addition of neodymium has a number of beneficial effects such as improving the reduction of microbial growth and decreasing the blood clotting.

Thus, the surface coating can be used to decrease microbial growth on an object, which at the same time is biocompatible, and tissue friendly for humans and animals.

The invention is an improvement/derivative of the materials defined for instance in U.S. Pat. No. 5,320,908. Differences include but are not limited to that the layer of silver in U.S. Pat. No. 5,320,908 is overlain by a layer comprising one or more platinum group metals or gold. In the present invention there are instead particles on the layer comprising silver. The metals in the particles are also different compared to the metals in the layer in U.S. Pat. No. 5,320,908. Further, different uses are provided in the present invention. In summary it is an improvement of the materials described in U.S. Pat. No. 5,320,908.

The silver coating is in one embodiment performed using a method selected from the group consisting of chemical vapour deposition, sputtering, and deposition of metal from a solution comprising a metal salt. A uniform layer essentially without clusters or agglomerates is in one embodiment the result of the deposition. In an alternative embodiment, the silver is coated in a non-uniform way so that the object may not be entirely coated. The deposition is carried out so that the layer has sufficiently good adhesion to the substrate, considering the intended use and the object to be coated. In one embodiment, the silver is coated in a patch-like way with silver patches covering a part of the object whereas other parts of the object are not coated.

The applied amount of the metal particles is expressed in $\mu g/cm^2$ and it must be realised that the metal particles do not form a covering layer, but instead are distributed particles or clusters on the silver layer. In one embodiment, the metal particles are uniformly distributed particles on the surface. In one embodiment, the metal particles are spaced apart so that they are not in contact with each other. In such an embodiment the metal particles are only in contact with the surface on which they are applied.

Without wishing to be bound by any particular scientific theory the inventors believe that there are several mechanisms of action contributing to the effects of the coating, i.e. that the coating is antimicrobial, biocompatible and at the same time decreases leakage of matter from the object below the coating and further at least in some embodiments reduces the blood clotting.

On a microscale the surface topography displays a certain roughness for instance because of the dispersed particles. This surface roughness may contribute to the properties of the surface, in particular in combination with other effects.

A coated object displays a negative surface charge, which can contribute in repelling negatively charged bacteria. Most bacteria are negatively charged. Zeta potential measurements have shown a negative surface charge in PBS under conditions common in the human body.

A galvanic effect from the different metals with different electrochemical potential create an electric current with the surrounding body fluids or other aqueous ionic solutions as electrolyte. The galvanic effect may contribute as well, not only by release of ions. The galvanic effect will lead to a very limited release or silver ions, but the amount of released silver ions is so low that it alone cannot explain the antimicrobial effect of the coating. Other factors have to contribute to this effect as well. It is an advantage of the invention that the release of silver ions is kept to a minimum.

Both silver and palladium are known to be able to act as catalysts for various reactions. The inventors speculate that there is a possibility that silver and/or palladium act as a catalyst facilitating for instance reactions that give antimicrobial properties, although this has not been verified experimentally.

The technical effects of the coating are most probably due to a combination of several mechanisms, which may include the above-described mechanisms.

The very low release of metal ions including silver ions is so low that it does not have any significant antimicrobial effect in itself. The antimicrobial effect cannot be attributed solely to release of toxic substances such as silver ions, since the released levels of ions cannot have any significant antimicrobial effects. Thus, the inventors believe that the antimicrobial properties are due to a combination of several mechanisms including the above mentioned effects. Bacterial adhesion and colonisation is suppressed by the surface coating and this give the antimicrobial effects.

Regarding the mechanisms of the decreased leakage of matter, the detailed mechanism is not entirely well understood, but from example 14, it can be concluded that the metal particles on the layer comprising silver play an important role.

Now there is described one embodiment of the present invention for preparation of the coating. In one embodiment, the method includes the following steps:
1. pre-treatment (optional)
2. rinsing (optional)
3. activation (optional)
4. deposition of silver
5. rinsing (optional)
6. deposition of metal particles
7. rinsing (optional)
8. drying (optional)

The pre-treatment and activation can be made in an aqueous solution of a stannous salt containing 0.0005 to 30 g/l of stannous ions. The pH is 1 to 4 and adjusted by hydrochloric and/or sulphuric acid. The treatment time is 2-60 minutes at room temperature. After the pre-treatment, the surface is rinsed in demineralised water, but not dried.

In addition to the above pre-treatment or instead of the above pre-treatment an additional pre-treatment can be carried out before the activation in the stannous salt. Such an additional pre-treatment is in one embodiment selected from the group consisting of treatment in alkali solution followed by neutralization in an acid solution, treatment in an NaOH solution followed by neutralization in HCl, treatment in an alkali solution upon heating to less than 90° C., treatment in an alcohol, and treatment in isopropanol.

Some polymeric objects are known to be difficult to coat in general such as for instance polytetrafluoroethylene (PTFE). For such difficult objects comprising for instance polytetrafluoroethylene (PTFE), polyether ether ketone (PEEK), polypropylene, and hydroxyapatite, an alternative pre-treatment can be used to improve the adhesion to the object. In one embodiment, a pre-treatment is performed before the coating. A plasticizer based on an aliphatic polyisocyanate is dissolved in a solvent. Suitable solvents include but are not limited to n-butyl acetate, isopropanol, and xylene. The dissolved plasticizer is applied to the object to be coated and then dried. The concentration of plasticizer is adapted so that the dried layer of plasticizer is only a few molecules thick in one embodiment. For such a thin coating, there are no essential changes in most of the physical properties of the object. When the surface has been cured, the coating can proceed. By using this pre-treatment good adhesion is obtained for difficult objects comprising polytetrafluoroethylene (PTFE), polyether ether ketone (PEEK) with carbon composite filler, nonwoven materials based on polypropylene, and hydroxyapatite. After the pre-treatment, the object is rinsed in demineralized water in one embodiment.

The activated/pre-treated and rinsed substrate is transferred to the deposition solution. The deposition solution has a pH of not less than 8. It includes a silver salt. In one embodiment of the present invention, the salt is silver nitrate (AgNO$_3$). The metal salt is used in an effective amount of no more than about 0.10 grams per litre, in one embodiment about 0.015 grams per litre is used. If the metal content is above about 0.10 grams per litre, the elemental metal may form in an undesirable way in the solution or on the container walls. If the metal content is below an effective amount, there is insufficient metal to form a layer in the desired time.

A second component of the deposition solution is a reduction agent that reduces the metal-containing salt to elemental metal. The reduction agent must be present in an amount sufficient to accomplish the chemical reduction. Acceptable reduction agents include but are not limited to formaldehyde, hydrazine sulphate, hydrazine hydroxide, and hypo phosphoric acid. In one embodiment of the present invention, it is present in an amount of about 0.001 millilitres per litre of solution. Too large a concentration of the reduction agent causes deposition of metal throughout the solution and on the container walls, while too small a concentration may result in an insufficient formation of metal on the substrate. A person skilled in the art can in the light of this description by routine experimentation determine the desired amount of reduction agent.

Another component of the deposition solution is a deposition control agent that is present in an amount sufficient to slow the deposition reaction to prevent the reduced metal from precipitating directly from solution as a fine metallic powder, or precipitating onto the walls of the container. Operable deposition control agents include but are not limited to inverted sugar, also known as invertose, succinic acid, sodium citrate, sodium acetate, sodium hydroxide, potassium hydroxide, sodium tartrate, potassium tartrate, and ammonia. The deposition control agent is in one embodiment present in an amount of about 0.05 grams per litre of solution. If too little is present, there may occur precipitation of too large metal clusters. If too much is present, the metal-containing salt may become too stable for the desired precipitation onto the substrate of interest.

The concentrations of the reduction agent and the deposition control agent are adjusted as necessary to achieve the desired results, depending upon the substrate material, the thickness of the film desired, the conditions of deposition, and the concentration of metal in the solution. For example, for thin films the metal salt concentration will be relatively low, as will the concentrations of the reduction agent and the deposition control agent. A person skilled in the art can in the light of this description by routine experimentation determine the desired amount of deposition control agent.

In preparing the deposition solution, each of the components of the solution are in one embodiment individually dissolved in demineralised water. The various pre-solutions are then mixed, and diluted where necessary, in the correct amounts to achieve the concentrations mentioned above.

The combination of a metal salt and reduction agent permits the metal to be reduced from the salt in a suitable state to be deposited upon the surface of the substrate. This method is particularly beneficial to achieve good adhesion of the completed metal film to the substrate surface. Good adhesion is important in nearly all uses.

The substrate surface is exposed to the deposition solution by any appropriate procedure. Dipping into the solution is carried out in one embodiment, but the solution may be applied by any convenient technique such as spraying or brushing. In one embodiment, the metal film deposits uniformly from the solution at a rate that may be controlled by the concentration of the metal salt. If a thin film is required, the temperature of deposition is maintained sufficiently low so that deposition is controllably slow. In an alternative embodiment, the silver is deposited non-uniformly, including deposits of silver particles and silver patches.

Other methods of applying a silver layer that acts as an electron-donating surface can also be applied in the present invention. Other ways of manufacturing a silver surface are chemical vapour deposition and sputtering.

The next step in the manufacturing method is deposition of metal particles.

In one embodiment colloidal suspensions of metals are used to obtain particles comprising palladium and at least another metal on the surface. The particles comprise a mixture of metals so that the desired composition is reached, i.e. the particles comprise an alloy of the desired composition of metals. The metal particles are deposited from a suspension of the desired particles. The composition of the metal particles in the suspension is adjusted according to the preferred value. The object with the silver surface is dipped in the suspension of metal particles for a period of time from about a few seconds to about a few minutes or longer.

The suspension of metal particles can be manufactured in several ways. In one embodiment, the suspension of metal particles is made from an aqueous solution of a metal salt, which is reduced under conditions such that metal particles of a desired size are formed. Mixing a suitable amount of metal salt, reducing agent and stabilising agent achieves this. The same reducing agents and stabilising agents as described above can be used when making the particle suspension. A person skilled in the art can in the light of this description by routine experimentation determine the desired amount of reducing agent and stabilising agent to get the desired particle size. In an alternative embodiment a commercially available colloidal suspension of metal particles is used. Metal particles of the desired composition are used to make the suspension.

In one embodiment, the suspension of metal particles is made by diluting with demineralised water a commercially available concentrated colloidal solution of metal particles comprising palladium and at least one metal selected from the group consisting of gold, ruthenium, rhodium, osmium, iridium, and platinum. The substrate is treated with the suspension for a period of time from about a few seconds to about a few minutes or longer. After the treatment the substrate is rinsed in a solvent or water such as demineralised water and left to dry in room temperature.

It is possible to adjust the particle size, the composition of the particles and the amount of particles to modify the surface properties of objects to which the coating is applied.

All percentages and ratios are calculated by weight unless otherwise clearly indicated.

Below are described a number of specific uses of the coating according to the present invention.

Contact Lenses

Contact lenses are often made of a polymeric material with significant water content. It is essential to avoid microbial growth on a contact lens. By using the method outlined above it is possible to coat a contact lens to prevent or reduce microbial growth. A coated contact lens will also be biocompatible, which is desirable. Further, a reduction of any substances from the contact lens during use is a desired property. Polymeric material can be coated according to the invention. The fact that the coating according to the invention can be applied to polymeric materials shows that the coating also can be applied to contact lenses of polymeric materials.

Pacemakers and Pacemaker Electrodes

Pacemakers to be inserted into the body of a human have to be biocompatible. At the same time it is desirable if they prevent microbial growth. Further the pacemaker should leak as little as possible of various substances to the surrounding tissues. A pacemaker or pacemaker electrode coated with the present coating has those desirable properties. A pacemaker or pacemaker electrode made of metal or any other material can successfully be coated according to the present invention.

Stents (Bare Metal and Drug Eluting)

Stents to be inserted into the body of a human should preferably be biocompatible. At the same time it is desirable if they prevent microbial growth. Further blood clotting caused by a stent should be as low as possible. Leakage of any material from the stent should also be minimized. A stent coated with the present coating has those desirable properties. Stents may be manufactured of metals or alloys and may successfully be coated with the coating according to the present inventions.

Dental Implants

Dental implants are advantageously both biocompatible and antimicrobial. Further the leakage of any substances to the body should be minimized. Dental implants can be made of titanium or any other materials. A dental implant coated according to the present invention is both biocompatible and antimicrobial and it further reduces leakage.

Rupture Nets, Mesh

Materials for nets and meshes can be coated. Such nets and meshes will be both antimicrobial and biocompatible which is an advantage within many applications together with the reduced leakage of matter to the surroundings.

Blood Centrifuge Equipment (in Contact with Blood)

In equipment intended for contact with blood the biocompatible and antimicrobial properties of the coating according to the present invention are desired. Further the reduced leakage of matter is also an advantage. The reduced blood clotting is also an advantage. Materials in contact with blood can be selected from a large number of materials. Blood centrifuge equipment comprising a substrate coated according to the present invention has improved properties regarding biocompatibility and antimicrobial properties as well as regarding blood clotting and leakage of substances.

Surgical Instruments

It is highly desirable that surgical instruments display antimicrobial properties. Materials often used for surgical instruments such as stainless steel and titanium can be coated. By using the coating according to the present invention the desired antimicrobial properties are achieved. Moreover the coating is also biocompatible. Further a reduced leakage of matter is also desirable for surgical instruments.

Gloves

It is often desired that gloves used for various purposes display antimicrobial properties. Moreover, gloves, which at the same time are tissue friendly and biocompatible, are desired for some applications. By coating gloves with the coating according to the present invention, the above-mentioned desired properties are achieved together with a reduced leakage of matter from the gloves. Polymeric materials can be coated according to the present invention with excellent results. In particular latex gloves can be coated to reduce the risk of allergic reactions.

Blood Bags

In blood bags intended for contact with blood the biocompatible and antimicrobial properties of the coating according to the present invention are desired. Reduced blood clotting and reduced leakage of matter to the blood is desirable. Materials for blood bags are most often polymeric materials. Polymeric materials can be coated according to the present invention with excellent results and examples of several polymeric materials are given above.

Artificial Heart Valves

For artificial heart valves the antimicrobial and biocompatible properties of the coating according to the present invention are highly desired together with the reduced leakage of matter and the reduced blood clotting. The coating can be applied successfully both to polymeric materials and metals that may constitute an artificial heart valve. The above-mentioned examples show that the coating can be applied to both polymeric materials and metals as well as alloys.

Central Venous Catheters

For catheters to be inserted into the body such as central venous catheters, antimicrobial properties are highly desired together with reduced leakage of matter and sometimes reduced blood clotting. Moreover objects to be inserted into the human body also should be biocompatible and tissue friendly. The coating according the present invention fulfils the requirements and has excellent properties for catheters. Materials used for catheters can be coated successfully with the coating according to the present invention.

Peripheral Venous Catheters

Regarding antimicrobial and biocompatible properties the requirements for peripheral venous catheters and central venous catheters are similar. Thus, the coating according to the present invention is also excellent for peripheral venous catheters.

Vascular Ports

Regarding vascular ports there is an infection risk and such vascular ports should be biocompatible. Further, a reduced leakage of matter a reduced blood clotting is desirable. Therefore, the coating according to the present invention is excellent for vascular ports so that they become antimicrobial and biocompatible. Materials used for vascular ports can successfully be coated with the coating according to the present invention.

Haemodialysis Equipment

For haemodialysis equipment, antimicrobial and biocompatible properties are important together with reduced blood clotting and reduced leakage of matter, thus making the coating according to the present invention very suitable.

Peritoneal Dialysis Equipment

For peritoneal dialysis equipment, the antimicrobial and biocompatible properties of the coating according to the present invention are very useful together with reduced leakage of matter. It is suitable to apply the coating according to the present invention to parts of such equipment.

Plasmapheresis Devices

For plasmapheresis devices, including catheters implanted for such purpose, the coating according to the present invention is suitable due to its antimicrobial and biocompatible properties together with the reduced blood clotting and reduced leakage of matter. Materials used in this context can successfully be coated according to the present invention.

Inhalation Drug Delivery Devices

Inhalation drug delivery devices advantageously display antimicrobial properties, which is achieved by coating suitable parts of the device with the coating according to the present invention. The biocompatible properties of the coating is also an advantage together with reduced leakage of matter.

Vascular Grafts (for Example Arterial Grafts)

Vascular grafts benefit from antimicrobial and biocompatible properties, which are achieved by the coating according to the present invention. Reduced leakage of matter and reduced blood clotting is also an advantage. The materials, which the grafts are made of, are suitable for coating according to the present invention.

Cardiac Assist Devices

Cardiac assist devices to be implanted into the body should be both biocompatible and antimicrobial. Reduced leakage of matter and reduced blood clotting is also an advantage. This is achieved by using a coating according to the present invention. Materials used for such devices are successfully coated using the present invention.

Wound Dressings

Wound dressings are preferably antimicrobial as well as biocompatible. Reduced leakage of matter and reduced blood clotting is also an advantage. This make them excellent objects for coating according to the present invention. Polymeric and fibrous material used for wound dressings are successfully coated according to the present invention.

Intermittent Catheters

Intermittent catheters as well as other catheters should preferably be both antimicrobial to avoid problems with infections, moreover they should also be biocompatible. Reduced leakage of matter and reduced blood clotting is also an advantage. The coating according to the present invention is excellent for catheters since it is both antimicrobial and biocompatible. Materials used for catheters can successfully be coated according to the present invention.

ECG Electrodes

ECG electrodes should preferably be both antimicrobial and biocompatible. Reduced leakage of matter and reduced blood clotting is also an advantage. ECG electrodes coated according to the present invention are both antimicrobial and biocompatible.

Peripheral Stents

Desired properties for peripheral stents are similar to those for stents as described above. Thus also peripheral stents can successfully be coated according to the present invention.

Bone Replacing Implants

Implants of different kinds such as bone replacing implants are preferably both antimicrobial and biocompatible. Reduced leakage of matter and reduced blood clotting is also an advantage. This is achieved by a coating according to the present invention.

Orthopaedic Implants

Orthopaedic implants as are very suitable to coat according to the present invention to render them antimicrobial and biocompatible. Reduced leakage of matter and reduced blood clotting is also an advantage. Examples of orthopaedic implants include but are not limited to hip replacements, total hip replacements, ceramic hip replacements, hip joint replacements, knee replacements, total knee replacements, and knee joint replacements.

Orthopaedic Devices (Screws, Pins, Staples, Suture Anchors Etc)

All kinds of orthopaedic devices such as screws, pins, staples, and suture anchors are preferably both antimicrobial and biocompatible. Reduced leakage of matter and reduced blood clotting is also an advantage. Such devices are made of materials, which successfully can be coated according to the present invention. Orthopaedic devices benefit from coating according to the present invention. One example of an orthopaedic device a screw of titanium coated according to the procedure described in example 13.

Tissue Replacing Implants

Implants of different kinds such as tissue replacing implants are advantageously both antimicrobial and biocompatible. Reduced leakage of matter and reduced blood clotting is also an advantage. This is achieved by a coating according to the present invention on the tissue replacing implants.

Intraocular Lenses

For intraocular lenses it is an advantage if they are antimicrobial and biocompatible. Reduced leakage of matter is also an advantage. This is achieved by coating according to the present invention. Intraocular lenses made of polymeric materials and other materials can successfully be coated according to the present invention.

Sutures

It is a great advantage for sutures to be antimicrobial and biocompatible. Reduced leakage of matter and reduced blood clotting is also an advantage. Sutures are therefore suitable for coating according to the present invention.

Needles

Needles that should be antimicrobial and/or biocompatible can successfully be coated according to the present invention to give the desired antimicrobial and biocompatible properties. Reduced leakage of matter and reduced blood clotting is also an advantage.

Drug Delivery Devices

Drug delivery devices, which shall be made antimicrobial and/or biocompatible and have reduced leakage of undesired matter to the surroundings, are advantageously coated according to the present invention.

Endotracheal Tubes

Endotracheal tubes are preferably antimicrobial as well as biocompatible. The polymeric materials that are used to manufacture endotracheal tubes are suitable for coating according to the present invention. Thus endotracheal tubes can successfully be coated according to the present invention to give the desired antimicrobial and biocompatible properties.

Shunts

For various kinds of shunts it is highly desirable that they display antimicrobial properties and that they are biocompatible. Reduced leakage of matter and reduced blood clotting is also an advantage. The materials that are used for shunts can successfully be coated according to the present invention and thus the shunt will get the desired properties.

Drains

Drains are preferably antimicrobial and biocompatible. Reduced leakage of matter and reduced blood clotting is also an advantage. Since the coating according to the present invention successfully can be applied to the materials from which drains are made, it is very suitable to apply the coating according to the present invention to drains.

Suction Devices

Suction devices should be antimicrobial and biocompatible. Reduced leakage of matter and reduced blood clotting is also an advantage. Since the coating according to the present invention successfully can be applied to the materials from which suction devices are made, it is very desirable to apply the coating according to the present invention to suction devices.

Hearing Aid Devices

Hearing aid devices are preferably antimicrobial and biocompatible. Reduced leakage of matter is also an advantage. The materials that hearing aid devices are made from can successfully be coated according to the present invention. Hearing aid devices are very suitable to coat according to the present invention.

Urethral Medical Devices

Urethral medical devices such as catheters, urethral stents and suprapubic stents are suitable to coat according to the present invention.

Artificial Blood Vessels

Artificial blood vessels are suitable to coat according to the present invention.

Other features of the invention and their associated advantages will be evident to a person skilled in the art upon reading the description and the examples. It is understood that the disclosed embodiments can be freely combined with all other embodiments as long as it is not clearly contradictory.

It is to be understood that this invention is not limited to the particular embodiments shown here. The following examples are provided for illustrative purposes and are not intended to limit the scope of the invention since the scope of the present invention is limited only by the appended claims and equivalents thereof.

EXAMPLES

Example 1

Prevention of Leakage of Allergens from Latex Foley Catheters.

For comparison both coated and uncoated Foley catheters of the same type and latex material were provided. Further a different type of Foley catheter made of latex without any proteins was provided as reference.

The Foley latex catheters to be coated were coated with the following method: A layer of silver was deposited on Foley catheters as substrates according to the following method. First the Foley catheters were cleaned and rinsed in demineralised water. The surface of the Foley catheters was activated by immersion in a solution of aqueous stannous chloride and then rinsed in demineralised water. The surface of the Foley catheters was then plated with a layer of silver by immersion in 3 deposition solutions comprising silver ions. This yielded a silver surface with an applied amount of 0.9 µg/cm². Particles consisting of 60 wt % palladium and 40 wt % gold were subsequently deposited on the first silver surface by immersion in a dilute suspension comprising metal particles of gold/palladium. The suspension of metal particles was made by reducing a gold salt and a palladium salt with a reducing agent and stabilising the suspension with a stabilising agent so that metal particles comprising gold and palladium was obtained. Each particle comprised both gold and palladium. The substrate was subsequently rinsed in demineralised water and dried.

An assay detecting leakage of allergens from the Foley catheters was made. The commercially available test kit Latex-T™ was used. The test kit detects latex proteins known to be responsible for allergic reactions to natural rubber products. There are two versions of the assay, red and blue respectively detecting different allergens common in latex.

Figure 3B:
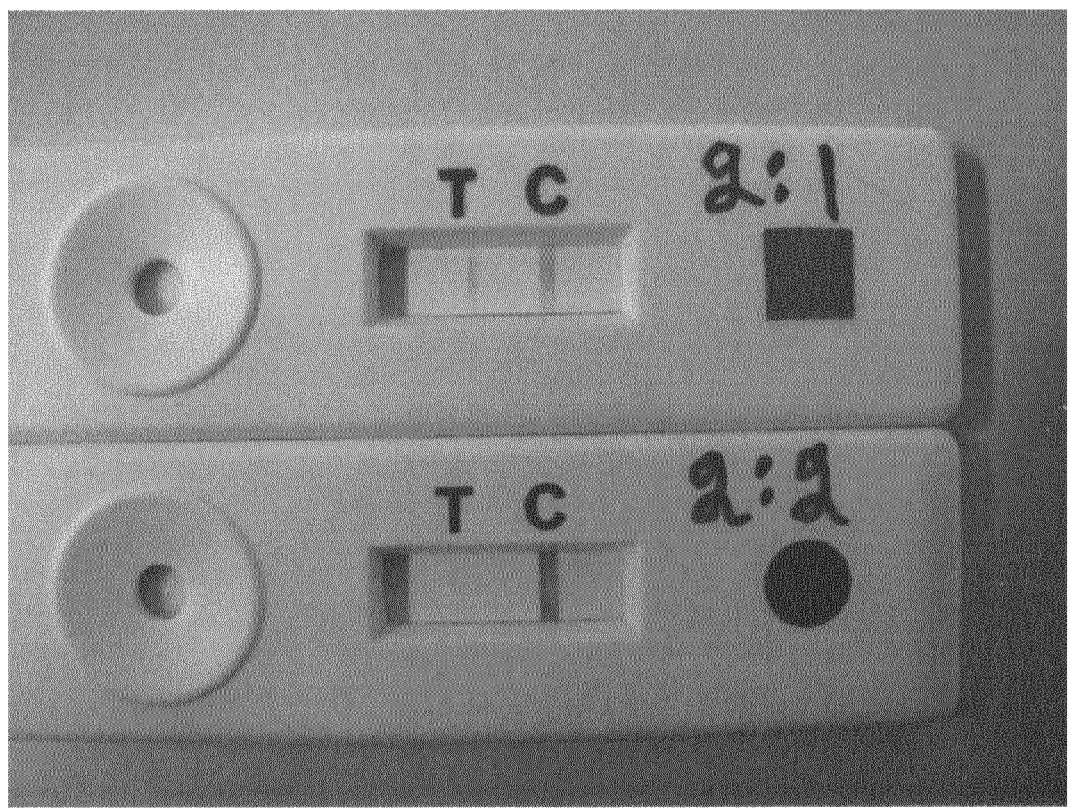
Figure 3C:
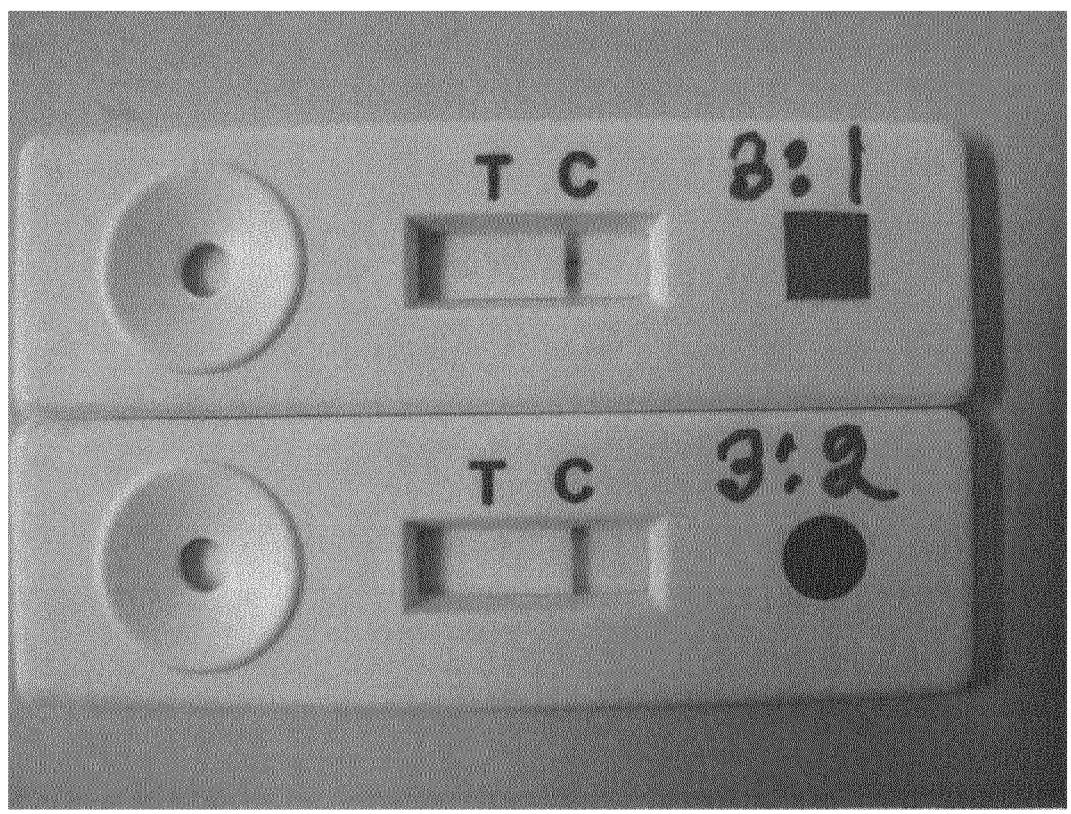

From each Foley catheter to be tested one piece of 4.5 cm was taken. Each piece to be tested was cut in smaller pieces and added to a bottle with the buffer solution provided with the test kit. Each bottle was shaken for 2 minutes. After that buffer 3 drops of buffer solution was added to the sample well of the assay device. The result was read after 20 minutes and the assay devices were photographed 20 minutes after the addition of the buffer solution to the assay devices. The photographs are shown in FIGS. 3a-c. It was verified that the control line appeared on all assay devices verifying that the assay had been functioning properly.

The tests and results are summarized in the table below:

| Sample No | Assay type | Sample | Result | FIG. |
|---|---|---|---|---|
| 1:1 | Red | Latex Catheter without proteins, uncoated | Negative, no visible reaction | 3a |
| 1:2 | Blue | Latex Catheter without proteins, uncoated | Negative, no visible reaction | 3a |
| 2:1 | Red | Latex Catheter with proteins, uncoated | Positive, a line can be seen | 3b |
| 2:2 | Blue | Latex Catheter with proteins, uncoated | Negative, no visible reaction | 3b |
| 3:1 | Red | Latex Catheter with proteins, coated | Negative, no visible reaction | 3c |
| 3:2 | Blue | Latex Catheter with proteins, coated | Negative, no visible reaction | 3c |

Assay type refers to the Red or Blue assay type supplied with the Latex-T™ test kit. The difference is that different allergens are detected in the different test types.

As can be seen the uncoated latex catheter gives a positive result in the red test, sample 2:1 in FIG. 3b. The corresponding identical sample but with the coating does not give a positive result, sample 3:1 in FIG. 3c. Thus it can be seen that the coating decreases the leakage of allergens from latex. According to the reference card for interpretation of the Latex-T™ test a line starts to appear when the concentration of the allergens detected by the red test increases above about 150-300 ng/ml. Without the coating the concentrations of allergens in the surrounding buffer is above this threshold but with the coating the concentration is below the threshold.

Example 2

Leakage of Ions from a Titanium-Nickel Alloy and its Corrosion Resistance.

Nitinol or nickel titanium consists of around equal parts of titanium and nickel. A study was made to evaluate the corrosion resistance of nitinol coated according to the present invention compared to untreated samples. The comparison was carried out on samples in the shape as tubing's as well as sheets. The coating was made with the following process, which provides a thin surface layer consisting of the noble metals gold, palladium and silver.

First nickel titanium (Nitinol) tubes/sheets were cleaned and rinsed in demineralised water. The surface of the tubes/sheets was activated by immersion in a solution of aqueous stannous chloride and then rinsed in demineralised water. The surface of the tubes/sheets was then plated with a layer of silver by immersion in 3 deposition solutions comprising silver ions. This yielded a silver surface with an applied amount of 1.6 µg/cm². Particles consisting of 23 wt % palladium and 77 wt % gold were subsequently deposited on the first silver surface by immersion in a dilute suspension comprising metal particles of gold/palladium. The suspension of metal particles was made by reducing a gold salt and a palladium salt with a reducing agent and stabilising the suspension with a stabilising agent so that metal particles comprising gold and palladium was obtained. Each particle comprised both gold and palladium. The tubes/sheets were subsequently rinsed in demineralised water and dried.

The test method that was performed according to ISO 10993-15:2000 (Identification and qualification of degradation products from metals and alloys).

The test solution was an isotonic aqueous solution of 0.9 wt % sodium chloride.

The pH of the solution before the tests was measured to 5.52. The samples were immersed in tubes consisting of borosilicate glass and the test solutions were kept at 37° C. and samples for measuring extracted after 7, 15, 30 and 60 days. Identical uncoated control samples were also measured.

The extracted samples were analyzed of the amount of nickel. By knowing the, surface area of the samples is was possible to calculate the amount of nickel so it corresponded to a release per $cm^2$ of the sample. The results are shown in the table below:

| Time | Uncoated nitinol tubing | Uncoated nitinol sheet | Coated nitinol tubing | Coated nitinol sheet |
| --- | --- | --- | --- | --- |
| 7 days | 0.03 | 0.04 | 0.00 | 0.00 |
| 15 days | 0.06 | 0.06 | 0.00 | 0.00 |
| 30 days | 0.08 | 0.07 | 0.00 | 0.01 |
| 60 days | 0.10 | 0.08 | 0.01 | 0.02 |

As can be seen from the table there is less release of nickel in the coated samples.

Example 3

Reduction of Bacterial Growth on Coated Nitinol.

Nickel titanium (Nitinol) was coated using the same method as in example 2 with the same amount of Ag and proportion of metals in the particles. The microbial adhesion of *S. aureus* was measured for an uncoated control sample and for a coated sample.

For the uncoated sample there were 2560 $CFU/cm^2$ and for the coated sample there were 285 $CFU/cm^2$. A reduction with about 88%. This verifies the ability of the coating to reduce the microbial adhesion to a surface.

Example 4

Blood Clotting on Coated Surfaces.

Figure 4:
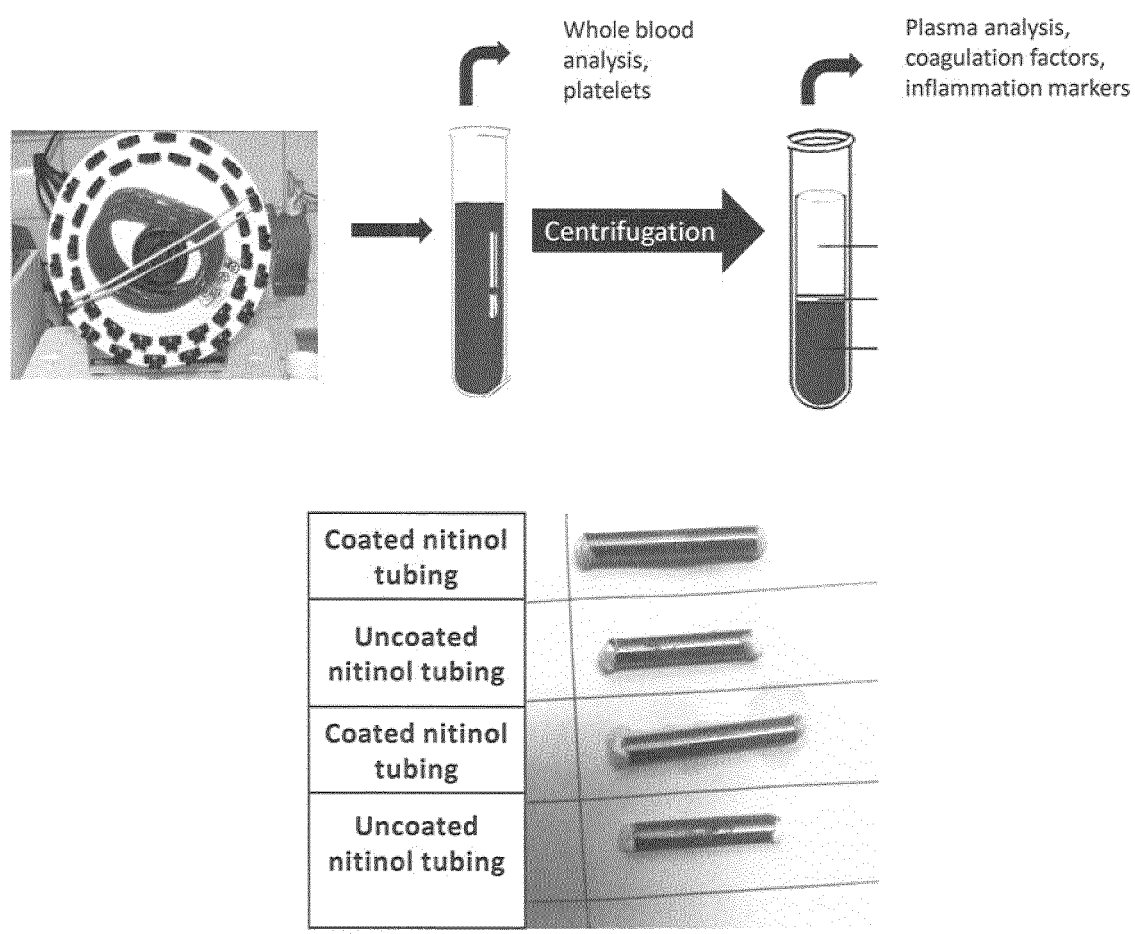
FIG. 4 shows the results of a test of blood clotting.

Nickel titanium (Nitinol) tubes were coated using the same method as in example 2 with the same amount of Ag and proportion of metals in the particles. The Chandler loop model was used for evaluating the blood compatibility. The test method allows the biocompatibility to be tested. The samples were brought into contact with fresh human blood. Afterwards the tendency to blood clotting was noticed. The results are shown in FIG. 4. As can be seen the coated samples show a low tendency to thrombosis/blood clotting.

Example 5

Blood Compatibility

Nickel titanium (Nitinol) tubes were coated using the same method as in example 2 with the same amount of Ag and proportion of metals in the particles.

The present investigation included one blood donors identified as BAC-12. Blood collection and handling was performed according to WI-2114 Chandler loop model.

TABLE 1

Placement of the Nitinol materials in the loop
Loop no. Material

Figure 5:
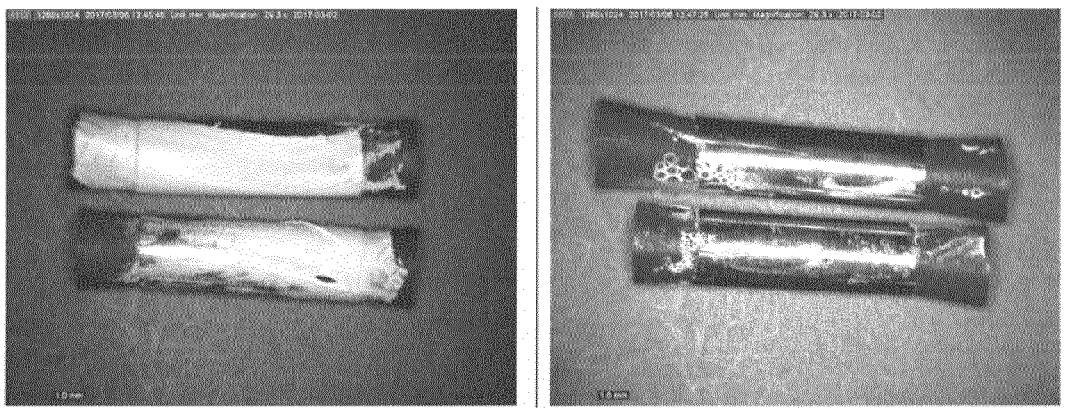
FIG. 5 shows the results of a test of blood clotting and deposition of proteins on surfaces.

1 Uncoated material
2 coated material
3 Uncoated material
4 coated material
5 Uncoated material
6 coated material
7 Loop Control N/A Protein deposition, coagulation and complement parameters were observed. The coagulation and complement parameter were analyzed following the WI-2114. After 60 minutes incubation time, the materials were removed from the loops and prepared for SEM analysis. The results are shown in FIG. 5. The difference between the materials is observed in FIG. 5. The control material (to the left) shows a greater amount of deposition of proteins on the surface while the material covered with the coating (to the right) is almost free of protein deposition. This phenomenon is directly related to the activities of coagulation and complement parameters, which are verified in the following table.

TABLE 2

Result of coagulation and complement parameters.

| Material | TAT ng/ml | C3a ng/ml | TCC ng/ml |
| --- | --- | --- | --- |
| Blood control | 7.8 | 51 | 95 |
| Uncoated control material | 881 ± 691 | 863 ± 276 | 397 ± 87 |
| Coated material | 339 ± 180 | 982 ± 295 | 334 ± 49 |
| Loop control | 36.1 | 479 | 256 |

By the results obtained from the TAT complex analysis, the control material generated almost two times more TAT complex than the coated material. No difference in the generation of C3a or TCC was not detected between analyzed materials. The values obtained for both the Blood control and the Loop Control are in accordance with previous observations.

Example 6

A Coated Metal Stent

An EverFlex™ metal stent was coated using the same method as in example 2 with the same amount of Ag and proportion of metals in the particles.

Blood collection and handling was performed according to WI-2114 Chandler loop model. The stents (coated and uncoated control) were brought into contact with the blood.

Figure 6:
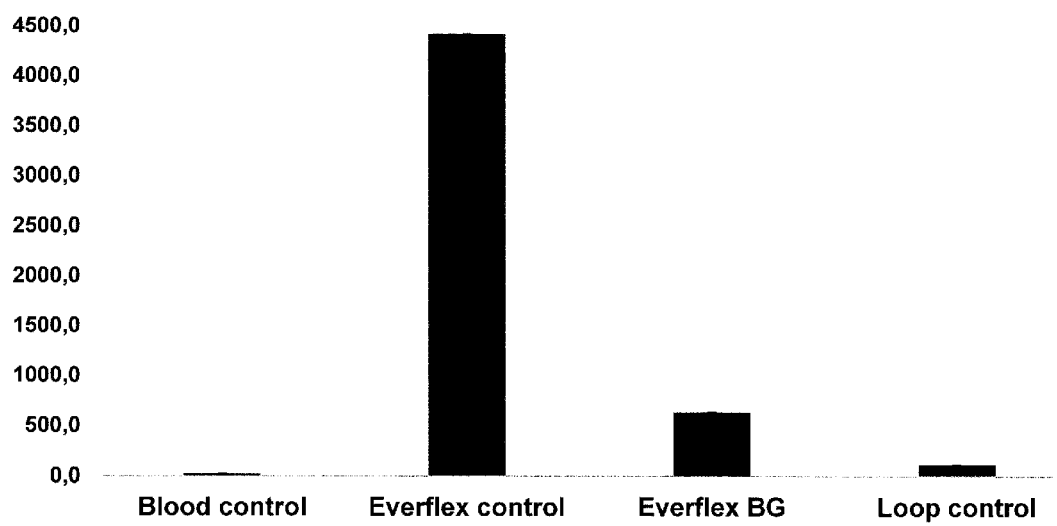
FIG. 6 shows the results of TAT measurements.

After incubation in the loop, blood was analysed for coagulation marker TAT. The TAT formation was measured and compared with an uncoated control sample. The values for TAT generation are shown in FIG. 6.

Figure 7:
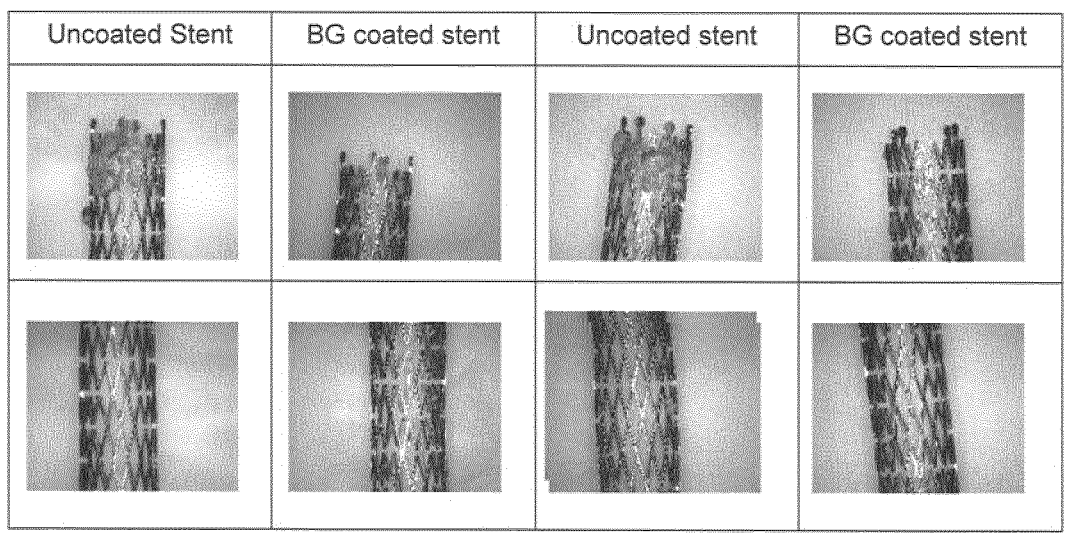
FIG. 7 shows a comparison of coated (BG coated) and uncoated stents regarding fibrinogen adsorption.

The coated and uncoated stents were also brought into contact with pig blood and the fibrin deposition was observed. For the uncoated samples, high fibrin deposition was noted, whereas the fibrin deposition on the coated stents were low, see FIG. 7.

Example 7

Effect of Rhodium

The stainless steel quality 304 is used in the medical device industry for applications as operation theatre tables, artificial valves for heart, precise tubing, containers for hazardous substances, and surgical forceps among others.

The steel quality is often chosen for its good feasibility where welding is needed as it has a very good resistance to intergranular corrosion. However, the material is less resistant to corrosion types as crevice corrosion, pitting and fretting compared to the stainless steel quality 316. (More resistant due to around 2% molybdenum in the alloy)

It should be noted that corrosion resistance and leakage of nickel is correlated so that a reduced leakage of nickel is associated with an improved corrosion resistance. Corrosion implies leakage of nickel.

To evaluate if the quality 304 could be improved in corrosion resistance (and nickel leakage) a comparing test was done with samples of pure 304, 304 coated with the combination Ag, Pd, Au, and 304 where the gold was replaced with rhodium.

First the samples were cleaned and rinsed in demineralised water. The surface of the samples was activated by immersion in a solution of aqueous stannous chloride and then rinsed in demineralised water. The surface of the samples was then plated with a layer of silver by immersion in 3 deposition solutions comprising silver ions. This yielded a silver surface with an applied amount of 1.5 µg/cm². Particles consisting of palladium and gold were subsequently deposited on the first silver surface by immersion in a dilute suspension comprising metal particles of gold/palladium. This gave an amount of 0.3 µg/cm² Au and 0.5 µg/cm² Pd on the surface as particles. The suspension of metal particles was made by reducing a gold salt and a palladium salt with a reducing agent and stabilising the suspension with a stabilising agent so that metal particles comprising gold and palladium was obtained. Each particle comprised both gold and palladium. The samples were subsequently rinsed in demineralised water and dried.

For some samples the particles of gold/palladium were replaced by particles of rhodium/palladium and no gold. The procedure was identical except that rhodium replaced gold and that the amount of metals in the particles were 0.3 µg/cm² Au and 0.7 µg/cm² Rh.

A soak test was done over time at 37° C. in physiological salt solution (0.9 wt % NaCl). In the solutions released nickel was measured and the results can be seen in table 1.

TABLE 1

| | Amount of Ni (µg/cm²) | | | | |
|---|---|---|---|---|---|
| Day | 1 | 3 | 7 | 14 | 28 |
| Untreated 304 | 0.11 | 0.19 | 0.36 | 0.99 | 1.63 |
| 304 with Ag/Pd/Au | <0.05 | 0.06 | 0.11 | 0.16 | 0.23 |
| 304 with Ag/Pd/Rh | <0.05 | <0.05 | <0.05 | 0.07 | 0.09 |

As can be seen the coating with Ag and particles of Pd/Au improves the corrosion resistance but the replacement of gold with rhodium (Ag and particles of Pd/Rh) creates an even more efficient protection and prevention of nickel leakage.

Using the so called Ahearn test for evaluation of the prevention of bacterial (microbial) growth showed 90-95% reduction of both types of coated 304 compared to the untreated samples. The test was carried out as described in Ahearn, D., Grace, D., Jennings, M. et al. Curr Microbiol (2000) 41: 120. It is thus verified that the antimicrobial properties remain also with Rh.

Example 8

Haemodialysis Catheters

Most of the hemodialysis catheters consists of polyurethane and to be able to apply the thin noble metal coating according to the invention and achieve enough adhesion one way is to etch the product before the coating process but this may under certain circumstances result in an unwanted discoloration. Instead, samples were treated with a 5 wt % solution of an aliphatic polyisocyanate in ethanol and dried in room temperature over night before the coating process was carried out. The aliphatic polyisocyanate is a plasticizer.

After the coating process performed as outlined in example 7, a noble metal combination with no discoloration was obtained. First with 1.1 µg/cm² Ag, 0.2 µg/cm² Au and 0.2 µg/cm² Pd. In another example there was in addition 0.1 µg/cm² of Nd (neodymium).

Samples were tested of blood compatibility comparing hemodialysis catheters with the only cured plasticizer with catheters added with the Ag/Au/Pd coating and also one with the coating added with Nd.

For the testing was used a Chandler Loop System which is suitable for testing thrombogenicity of biomaterials. The model is an in vitro model using fresh blood from a donor and rotated at body temperature with the blood in contact with the test sample. As a marker for the thrombin generation the thrombinantithrombin-III complex TAT was measured.

| | TAT value |
|---|---|
| Sample with only plasticizer | 143 |
| Sample with Ag/Au/Pd | 46 |
| Sample with Ag/Au/Pd/Nd | 17 |

The normal three combination of Ag/Au/Pd shows a reduction in thrombosis, but this is improved with the addition of a small amount of Nd.

The prime effect of the noble metal coating is to prevent bacterial growth and this is measured by using the Ahearn test which enables a calculation of the percentage of bacterial growth reduction compared to the uncoated substrate. The test was carried out as described in Ahearn, D., Grace, D., Jennings, M. et al. Curr Microbiol (2000) 41: 120.

To verify that this effect was not affected by the addition of Nd this measurement was carried out and the reduction in the Ag/Au/Pd sample was 95.3% and in the sample with Nd added 95.5% which shows essentially the same effect.

Example 9

Knee and Hip Implants

An alloy named as ASTM F 75 is used for knee and hip implants and in its cast form also as total hip prosthesis. The alloy may consist of 57-65 wt % cobalt; 27-30 wt % chromium; 5-7 wt % molybdenum and up to 0.5 wt % nickel. It has been reported that bio corrosion may occur which can cause a release of metal ions. Especially nickel and cobalt are responsible for allergic reactions.

A comparing test was done on pure substrates of the above-mentioned alloy and the same alloy coated with 1.6 µg/cm² Ag and 0.3 µg/cm² each of Au and Pd. The coating was applied as in example 7. The test solution was the normal standard for testing in contact with blood, a PBS solution (phosphate-buffer saline) consisting of 8 g/l NaCl, 2.7 g/l KCl, 1.42 g/l Na₂HPO₄, 0.24 g/l KH₂PO₄. This test solution is used among others for the corrosion testing of implantable devices.

The test samples were immersed in the solution for 30 days at 37° C. and the release of metal ions was measured after that time. The values were converted to µg/cm² calculated on the surface of the object.

|  | Co | Cr | Ni |
|---|---|---|---|
| Uncoated samples | 0.11 | 0.05 | 0.03 |
| Coated samples | 0.01 | 0.01 | 0.00 |

As can be seen the coating prevents most of the metal ion release.

Example 10

Dental Implants

Dental implants are often made of a pure titanium or titanium alloys. The most common titanium alloy for this purpose is according to ASTM grade 5, which normally is described as Ti-6Al-4V which means that it contains 6% aluminum and 4% vanadium.

The environment in the body for dental implants is very tough mainly because of the composition of saliva which creates an acidic surrounding and if there is a release of metal ions problems can occur as immunological response, inflammatory response infection or toxicity. Corrosion products that are formed in the interaction between the metal and its environment have also an impact on the biocompatibility.

Dental screws of the composition mentioned above were tested in artificial saliva of the composition Methyl-p-hydroxybenzoate 2.00 g/l, Sodium Carboxymethyl Cellulose 10.00 g/l, KCl 0.625 g/l, MgCl₂·6H₂O 0.059 g/l, CaCl₂·2H₂O 0.166 g/l, K₂HPO₄ 0.804 g/l, KH₂PO₄ 0.326 g/l. The pH was adjusted to 6.6 with potassium hydroxide.

The screws with coating contained 1.8 µg/cm² Ag and 0.3 µg/cm² each of Pd and Au. The coating was applied as in example 7. A comparison was made with uncoated screws.

The test was carried out at 37° C. during a period of 28 days and measurements were made at intervals of one week on the amount of titanium. The values are presented as microgram/liter.

|  | 7 days | 14 days | 28 days |
|---|---|---|---|
| Uncoated sample | 0.06 | 0.09 | 0.14 |
| Au/Pd/Ag coated sample | 0.00 | 0.01 | 0.02 |

As can be seen from the measurement the coating strongly reduces the dissolution of titanium.

Example 11

Vascular Grafts

Vascular grafts are often made of PTFE which is a material that is difficult to apply a coating on that is sufficient adherent to the substrate but also to obtain suitable amount of noble metals to prevent microbial growth.

Samples of vascular grafts were treated with a plasticizer in the same way as in example 8.

After the coating process performed as outlined in example 7, a noble metal combination was obtained. First with 1.1 µg/cm² Ag, 0.2 µg/cm² Au and 0.2 µg/cm² Pd. In another example there was in addition 0.1 µg/cm² of Nd (neodymium).

To see if the prevention of thrombosis could be improved by the addition of Nd, samples were run in the Chandler loop model both with and without Nd as well as samples with only plasticizer as control. The formation of TAT was analysed with following results

| Control | 55 µg/l |
|---|---|
| Sample with Ag/Au/Pd coating | 42 µg/l |
| Sample with Ag/Au/Pd/Nd coating | 29 µg/l |

The lower TAT values indicates a lower tendency to thrombosis formation.

Example 12

Surgical Mesh

A mesh is similar to a net and can be used for many different purposes as for example filters, screens for radiation, barriers etc. In this case we refer to surgical mesh which use is to act as a reinforcing structure in the human or animal body.

When a surgical mesh is placed in the body during surgery it is very important that the material in the mesh prevents microbial growth as well as maintaining as good antithrombogenic properties as possible. To evaluate if the noble metal coating based on Ag, Au and Pd could be improved further a test was made by comparing with a mesh where Nd was added to the coating.

As base material was used a mesh consisting of monofilament polypropylene used for hernia repairs (rupture nets) and for chest wall reinforcement.

Before the noble metal coating procedure the mesh was pretreated at 40° C. for 10 min in 8 wt % sodium hydroxide and after that neutralized in 5 wt % hydrochloric acid.

After the pre-treatment, the samples were cleaned and rinsed in demineralised water. The surface of the samples was activated by immersion in a solution of aqueous stannous chloride and then rinsed in demineralised water. The surface of the samples was then plated with a layer of silver by immersion in 3 deposition solutions comprising silver ions. This yielded a silver surface with an applied amount of 2.2 µg/cm². Particles consisting of palladium and gold were subsequently deposited on the first silver surface by immersion in a dilute suspension comprising metal particles of gold/palladium. This gave an amount of 0.4 µg/cm² Au and 0.4 µg/cm² Pd on the surface as particles. The suspension of metal particles was made by reducing a gold salt and a palladium salt with a reducing agent and stabilising the suspension with a stabilising agent so that metal particles comprising gold and palladium was obtained. Each particle comprised both gold and palladium.

For some samples, Nd was added in the particles, by adding a neodymium salt together with the gold salt and palladium salt. Then the each of the particles comprised Au, Pd, and Nd. In the particles also comprising Nd the amounts in the particles were Au 0.4 µg/cm$^2$, Pd 0.4 µg/cm$^2$, and Nd 0.12 µg/cm$^2$.

The samples were subsequently rinsed in demineralised water and dried.

The samples were brought into contact with blood. In contact with blood the time when the clotting started was measured. A reference value here is 990 seconds and for a good antithrombogenic property the time has to be as close as possible to this value. The measurements were as follows:

|  | Clotting time (seconds) |
| --- | --- |
| Untreated mesh | 450 |
| Mesh coated Ag/Au/Pd | 750 |
| Mesh coated Ag/Au/Pd/Nd | 930 |

As can be seen the addition of a small amount of Nd improves the effect of preventing thrombosis.

Example 13

Suture Materials

Surgical site infections due to suture associated microbiological biofilms are common and there has been estimations that up to 5% of all procedures using sutures leads to some sort of infection.

As suture material there is a variety of materials such as nylon, polypropylene, polyester, silk, polyglycolic acid, polydioxanone among others. Studies of different suture materials have shown around the same ratio of infections irrespective of suture material.

To investigate if the present coating could help with preventing microbial growth and improving blood compatibility on different materials three different suture materials were chosen. As test material pieces of nylon, polypropylene and braided silk were chosen. Comparison was made between uncoated pieces as control, the standard coating comprising gold, silver and palladium and also samples with the addition of a small amount of neodymium.

To be able to obtain around the same amounts of metals on the different materials the samples had to be pretreated in different ways.

Nylon sutures were washed for 5 minutes in 5 wt % sodium hydroxide at room temperature and then neutralized with 5 wt % hydrochloric acid.

Polypropylene sutures were immersed in 8 wt % potassium hydroxide at 50° C. for 10 minutes.

Braided silk was washed at room temperature with isopropanol for 2 minutes and then dried over night at room temperature.

After the pretreatment the suture pieces were treated in the same way with a coating processes with and without neodymium respectively. The coating process was as described in example 7.

All materials received a silver pick up in the range 1.2-1.5 µg/cm$^2$ Ag. The amount of particles on the surface corresponded to 0.3 µg/cm$^2$ Pd and 0.3 µg/cm$^2$ Au. For the samples where neodymium was present the amount was 0.05 µg/cm$^2$ Nd.

For the blood compatibility the Chandler loop test was used, see FIG. 4 and for the reduction of bacterial growth the Ahearn test was used. as described in Ahearn, D., Grace, D., Jennings, M. et al. Curr Microbiol (2000) 41: 120.

Results:

| Material | TAT value | Reduction of bacterial growth (%) |
| --- | --- | --- |
| Nylon uncoated | 96 | 0 |
| Nylon Ag/Pd/Au | 46 | 95 |
| Nylon Ag/Pd/Au/Nd | 35 | 97 |
| Polypropylene uncoated | 130 | 0 |
| Polypropylen Ag/Pd/Au | 55 | 96 |
| Polypropylen Ag/Pd/Au/Nd | 42 | 96 |
| Braided silk uncoated | 165 | 0 |
| Braided silk Ag/Pd/Au | 54 | 97 |
| Braided silk Nylon Ag/Pd/Au/Nd | 46 | 100 |

The results for the different materials show the same trend with a large reduction in bacterial growth and a reduction in the blood clotting formation (tat value) where the addition of neodymium is an improvement.

Example 14

Corrosion protection of implant materials A problem that can occur with metallic implanted devices is leakage of metal ions such as nickel, cobalt, titanium, chromium. The leakage is due to chemical reactions between the implant surface and substances in the surrounding body environment and it can cause adverse events such as inflammatory reactions. There are many reports of different problems related to corrosion of implanted devices. Even if no problems occur it is desirable to minimize the leakage as a general precaution. It is remarkable that the thin noble metal layer (Ag/Pd/Au) which can be as thin as down to only 5-20 atoms can reduce the leakage of metal ions from implanted metallic alloys. A thicker layer would naturally prevent corrosion but the intended use of the thin coating to prevent bacterial growth and at the same time act tissue friendly would in that case get lost.

As can be seen from the experimental data shown in Table 3 and Table 4, a combination of the noble metals is necessary to prevent the release of metal ions. If using only Ag there will be a release of silver ions which can kill bacteria and in that case there will be an unwanted pharmaceutical effect from the silver ions as well as a decrease in the biocompatibility.

Comparison of uncoated, Ag/Pd/Au coated and only Ag coated substrates. Substrate material stainless steel grade 304L (Ni 9.25 wt %; Cr 19 wt %). Test solution physiological salt solution (0.9 wt % NaCl) at 37° C. The Ag/Pd/Au layer had the composition Ag 1.5, Pd 0.5, Au 0.3 measured as µg/cm$^2$. Samples with only silver was 1.7 µg/cm$^2$ Ag. The samples were coated following the method outlined in example 7.

TABLE 3

| Days<br>Metal | 1<br>Ag | 1<br>Ni | 3<br>Ag | 3<br>Ni | 7<br>Ag | 7<br>Ni | 14<br>Ag | 14<br>Ni |
|---|---|---|---|---|---|---|---|---|
| Uncoated 304 L | — | 0.11 | — | 0.19 | — | 0.36 | — | 0.99 |
| Ag/Pd/Au Coated 304 L | 0.04 | <0.05 | 0.09 | 0.06 | 0.08 | 0.11 | 0.11 | 0.16 |
| Ag Coated 304 L | 0.29 | 0.06 | 0.41 | 0.10 | 0.55 | 0.15 | 0.67 | 0.29 |

Conclusion: The combination of the metals Ag/Pd/Au which is used for preventing bacterial growth also very much reduces the leakage of metal ions from implantable metallic alloys despite the thin layer thickness. Using only Ag in this range shows higher release of Ag as well as higher release of metal ions from the substrate. Thus it can be concluded that the particles on the silver layer reduce the leakage.

Comparison of uncoated, Ag/Pd/Au-coated and Ag-coated surface. Substrate material ASTM F 75 (28.5 wt % Cr, 6 wt % Mo, 0.25 wt % Ni, 0.2 wt % Fe, smaller amounts of various other elements and the balance Co). Test solution 0.01 M HCl (pH 2.0) corresponds to the pH value in gastric acid. Test run at 37° C. The composition of the coating was Ag 1.5 µg/cm$^2$, Pd 0.4 µg/cm$^2$, and Au 0.04 µg/cm$^2$. With only silver the value was 1.6 µg/cm$^2$. The samples were coated following the method outlined in example 7.

TABLE 4

| Days<br>Metal | 1<br>Ag | 1<br>Co | 1<br>Cr | 1<br>Ni | 7<br>Ag | 7<br>Co | 7<br>Cr | 7<br>Ni | 14<br>Ag | 14<br>Co | 14<br>Cr | 14<br>Ni |
|---|---|---|---|---|---|---|---|---|---|---|---|---|
| Uncoated ASTM F75 | — | 0.09 | 0.03 | 0.01 | — | 0.23 | 0.08 | 0.04 | — | 0.35 | 0.12 | 0.07 |
| Ag/Pd/Au Coated ASTM F75 | 0.02 | 0.01 | ≤0.01 | ≤0.01 | 0.05 | 0.03 | 0.02 | ≤0.01 | 0.07 | 0.05 | 0.03 | 0.01 |
| Ag Coated ASTM F75 | 0.12 | 0.07 | 0.03 | 0.01 | 0.27 | 0.17 | 0.10 | 0.03 | 0.59 | 0.31 | 0.15 | 0.06 |

Conclusion: The thin layer of the noble metals Ag/Pd/Au prevents most of the release of the metal ions from the substrate. When only silver is used the release is higher and in addition more Ag is dissolved and released as silver ions.

Example 15

Bactiguard Coating on Different Metal Medical Device Applications.

Analogous with previous examples the device materials were first treated in a bath containing stannous ions and after rinsing immersed in baths containing silver ions. Depending on the material the concentration and time in the bath was varied. After rinsing the last step was immersing in a solution containing palladium and gold and for comparative purposes some samples were also treated in a bath containing neodymium ions in addition to the palladium and gold.

The evaluation of the tendency to thrombosis was evaluated by using a Chandler loop model and the blood donors was from a small group of 5 persons often used for this test and therefore the results can be considered as comparable. All coated samples were also tested for bacterial growth prevention using the Ahearn test. All coated samples exceeded 90% reduction.

Titanium Implant Material 3 cm long pieces of Ti6Al4V (ASTM TiGr5) which is a common material for trauma implants were treated in the process and measurement afterwards showed a silver amount of 1.3 µg/cm$^2$. The amount of Pd was 0.7 µg/cm$^2$, Au 0.05 µg/cm$^2$. In the sample containing Nd there was only added 0.01 µg/cm$^2$.

To evaluate the blood clotting (thrombosis) the Chandler loop model was used and the tendency of blood clotting was determined by measuring the TAT values as well as with visual inspection.

Uncoated Ti6Al4V TAT 4089 ng/ml
Coated with Pd/Au/Ag TAT 268 ng/ml
Coated with Pd/Au/Ag/Nd TAT 196 ng/ml As can be seen above there is a huge reduction in the TAT values and in the visual inspection clotting can only be seen on the uncoated samples.

Stainless Steel 316L (Medical Grade)

The material is often used in guidewires, implants and surgical instruments.

Rods of 30 mm length were used and treated as described above. The amount of silver deposited on the surface was 0.9 µg/cm$^2$, Pd 0.5 µg/cm$^2$, Au 0.1 µg/cm$^2$. In the sample containing Nd the amount was 0.03 µg/cm$^2$.

The results from the Chandler loop can be seen below.
Uncoated 316L TAT 4943 ng/ml
316L coated with Pd/Au/Ag TAT 221 ng/ml
316L coated with Pd/Au/Ag/Nd TAT 137 ng/ml There is a high reduction in thrombosis which the TAT values shows and with the small addition of neodymium a further reduction can be seen. The visual inspection shows only clotting on the control samples.

The invention claimed is:

1. A coated object with decreased leakage of matter from the object to a surrounding, comprising:
    the object; and
    a coating applied on the object, said coating comprising
        a layer applied patch-wise on the object, the layer comprising silver, and
        metal particles applied on the layer, said metal particles comprising palladium and at least one metal selected from the group consisting of gold, ruthenium, rhodium, osmium, iridium, niobium, neodymium and platinum, wherein the amount of the metal particles is in the range of 0.01-8 µg/cm$^2$,
        wherein the application of the coating to the object reduces leakage of matter from the object.

2. The coated object according to claim 1, wherein said layer comprises silver in an amount in the range of 0.05-12 µg/cm$^2$.

3. The coated object according to claim 1, wherein said layer comprises silver in an amount below 8 µg/cm$^2$.

4. The coated object according to claim 1, wherein said layer comprises silver in an amount in the range of 0.05-4 µg/cm$^2$.

5. The coated object according to claim 1, wherein the object comprises at least one metal.

6. The coated object according to claim 5, wherein the at least one metal is selected from the group consisting of stainless steel, medical grade steel, titanium, medical grade titanium, cobalt, nickel, chromium, and mixtures thereof.

7. The coated object according to claim 5, wherein the at least one metal is an alloy comprising nickel and titanium.

8. The coated object according to claim 1, wherein the object comprises at least one polymer.

9. The coated object according to claim 8, wherein the at least one polymer is selected from the group consisting of latex, vinyl, polymers comprising vinyl groups, polyurethane urea, silicone, polyvinylchloride, polypropylene, styrene, polyurethane, polyester, copolymerisates of ethylene vinyl acetate, polytetrafluoroethylene, polyether ether ketone, polystyrene, polycarbonate, polyethylene, polyacrylate, polymethacrylate, acrylonitrile butadiene styrene, polyamide, polyimide, and mixtures thereof.

10. The coated object according to claim 8, wherein the polymer is latex.

11. The coated object according to claim 1, wherein the object comprises at least one selected from apatite and hydroxyapatite.

12. The coated object according to claim 1, wherein the amount of the metal particles is in the range of 0.01-4 µg/cm$^2$.

13. The coated object according to claim 1, wherein the amount of the metal particles is 10-30% of the amount of silver in the layer, calculated by weight.

14. The coated object according to claim 1, wherein the metal particles are separated particles, not in contact with each other.

15. The coated object according to claim 1, wherein the ratio, by weight, of palladium to non-palladium metals in the metal particles is from about 0.5:99.5 to about 99.8:0.2.

16. The coated object according to claim 1, wherein the ratio, by weight, of palladium to non-palladium metals in the metal particles is from about 2:98 to about 95:5.

17. The coated object according to claim 1, wherein the metal particles, in addition to palladium, comprise gold.

18. The coated object according to claim 1, wherein the metal particles in addition to palladium, comprise gold so that the ratio calculated by weight between palladium and gold is in the range of 0.8-1.2.

19. The coated object according to claim 1, wherein the metal particles, in addition to palladium, comprise rhodium.

20. The coated object according to claim 1, wherein the metal particles have a size in the range of 10-10000 Å.

21. The coated object according to claim 1, wherein the metal particles have a size in the range of 100-600 Å.

22. The coated object according to claim 1, wherein the object is at least one selected from the group consisting of a catheter, a glove, an implant, a pacemaker, a stent, a dental implant, a rupture net, a surgical instrument, a blood bag, an artificial heart valve, a central venous catheter, a peripheral venous catheter, a vascular port, a haemodialysis equipment, a peritoneal dialysis equipment, a plasmapheresis device, an inhalation drug delivery device, a vascular graft, a cardiac assist device, a wound dressing, an intermittent catheter, an ECG electrode, a peripheral stent, a bone replacing implant, an orthopaedic implant, an orthopaedic device, a tissue replacing implant, an intraocular lens, a suture, a needle, a drug delivery device, an endotracheal tube, a shunt, a drain, a suction device, a hearing aid device, an urethral medical device, and an artificial blood vessel.

23. The coated object according to claim 1, wherein the surrounding comprises a solution.

24. The coated object according to claim 1, wherein the surrounding comprises human or animal tissue.

25. The coated object according to claim 1, wherein the matter of which the leakage is to be reduced, is at least one selected from the group consisting of proteins and ions.

26. A coated object with decreased leakage of matter from the object to a surrounding, comprising:
the object; and
a coating applied on the object, said coating comprising
a layer comprising silver, and
metal particles applied on the layer, wherein the metal particles comprise palladium and at least one of niobium or neodymium, wherein the amount of the metal particles is in the range of 0.01-8 µg/cm$^2$.

27. The coated object according to claim 26, wherein the neodymium is present in an amount corresponding to 0.002-0.5 µg/cm$^2$.

28. The coated object according to claim 26, wherein the coating also reduces the risk of blood clotting when the coating is in contact with blood.

29. A surface coating for use in at least one of prevention, alleviation and treatment of symptoms at least partially caused by leakage from an object, said surface coating is applied on the object, said surface coating comprising a layer applied patch-wise on the object, the layer comprising silver, said surface coating further comprising metal particles applied on the layer, said metal particles comprising palladium and niobium and wherein the amount of the metal particles is in the range of 0.01-8 µg/cm2.

* * * * *